(12) United States Patent
Gualfetti et al.

(10) Patent No.: US 6,635,465 B1
(45) Date of Patent: Oct. 21, 2003

(54) MUTANT EGIII CELLULASE, DNA ENCODING SUCH EGIII COMPOSITIONS AND METHODS FOR OBTAINING SAME

(75) Inventors: Peter Gualfetti, San Francisco, CA (US); Colin Mitchinson, Half Moon Bay, CA (US); Traci H. Ropp, San Francisco, CA (US)

(73) Assignee: Genencor International, Inc., Palo Alto, CA (US)

( * ) Notice: Subject to any disclaimer, the term of this patent is extended or adjusted under 35 U.S.C. 154(b) by 34 days.

(21) Appl. No.: 09/632,575

(22) Filed: Aug. 4, 2000

(51) Int. Cl.$^7$ ............... C12N 9/42; C11D 3/386
(52) U.S. Cl. ............ 435/209; 510/392; 241/28; 426/656
(58) Field of Search ............ 435/209; 510/392; 241/28; 426/656

(56) References Cited

U.S. PATENT DOCUMENTS

| | | | |
|---|---|---|---|
| 4,760,025 A | 7/1988 | Estell et al. | 435/222 |
| 4,832,864 A | 5/1989 | Olson | 252/174.12 |
| 5,185,258 A | 2/1993 | Caldwell et al. | 435/220 |
| 5,246,853 A | 9/1993 | Clarkson et al. | 435/263 |
| 5,254,283 A | 10/1993 | Arnold et al. | 252/174.12 |
| 5,290,474 A | 3/1994 | Clarkson et al. | 252/174.12 |
| 5,475,101 A | 12/1995 | Ward et al. | 536/23.74 |
| 6,187,577 B1 | 2/2001 | Jones et al. | 435/209 |
| 6,268,328 B1 * | 7/2001 | Mitchinson et al. | 510/392 |

FOREIGN PATENT DOCUMENTS

| | | |
|---|---|---|
| EP | 220 016 B1 | 8/1991 |
| EP | 271 004 B1 | 4/1993 |
| GB | 1358599 | 7/1974 |
| GB | 2075028 A | 11/1981 |
| GB | 2 094 826 A | 9/1982 |
| GB | 2095275 A | 9/1982 |
| WO | WO 92/06209 | 4/1992 |
| WO | WO 94/14953 | 7/1994 |
| WO | WO 94/28117 | 12/1994 |
| WO | WO 98/31821 | 7/1998 |
| WO | WO 99/31255 | 6/1999 |
| WO | WO 00/09707 | 2/2000 |
| WO | WO 00/14206 | 3/2000 |
| WO | WO 00/14208 | 3/2000 |
| WO | WO 00/37614 | 6/2000 |
| WO | WO 01/47956 A2 | 7/2001 |
| WO | WO 02/12464 A2 | 2/2002 |
| WO | WO 02/12465 A2 | 2/2002 |
| WO | WO 02/12466 A2 | 2/2002 |

OTHER PUBLICATIONS

Accession No. Q12679, 1997.*
Accession No. S12610, 1994.*
.Accession No. 013454, 1998.*
Accession No. P22669, 1991.*

Altschul, S. et al., "Basic Local Alignment Search Tool," *J. Mol. Biol.*, Vol 215, No. 3, pp. 403–410, 1990.

Ausubel, Frederick et al., *Short Protocols in Molecular Biology, Current Protocols in Molecular Biology*, 2$^{nd}$ ed., Greene Publishing Associates & John Wiley & Sons. New York, N.Y. 1992, 12–24 to 2–38.

Bergés, T. et al., "Isolation of uridine auxotrophs from *Trichoderma reesei* and efficient transformation with the cloned ura3 and ura5 genes," *Curr. Genet.* vol. 19, No. 5, pp. 359–365, 1991.

Berka, Randy M. et al., "The Development of Gene Expression Systems for Filamentous Fungi," *Biotech. Adv.* 7:127–154, 1989.

Burley, S.K. et al., "Aromatic–Aromatic Interaction: A Mechanism of Protein Structure Stabilization," *Science* 229:23–29, 1985.

Eriksson, A. E. et al., "Response of a Protein Structure to Cavity–Creating Mutations and its Relation to the Hydrophobic Effect," *Science* vol. 255, pp. 178–183, 1992.

Georis, Jacques et al., "An additional aromatic interaction improves the thermostability and thermophilicity of a mesophilic family 11 xylanase: Structure basis and molecular study," Protein Science, Cambridge University Press, 9:466–475, 2000.

Gloss, L. M., et al., "Urea and Thermal Equilibrium Denaturation Studies on the Dimerization Domain of *Escherichia coli* Trp Repressor" *Biochem.* vol. 36, No. 19, pp. 5612–5623, 1997.

Henikoff, Steven, et al., *Proc. Natl. Acad. Sci. USA*, 89:10915–10919, 1989.

Hreggvidsson, Gudmundur O., et al., "An Extremely Thermostable Cellulase from the Thermophilic Eubacterium *Rhodothemus marinas*," *Appl. Environ. Mircob.* vol. 62, No. 8, pp. 3047–3049, 1996.

Karlin, S., et al., "Applications and statistics for multiple high–scoring segments in molecular sequences," *Proc. Natl. Acad. Sci. USA* vol. 90, pp. 5873–5877, 1993.

Kellis, J. et al., "Contribution of hydrophobic interactions to protein stability," *Nature*, vol. 333, pp. 784–786, 1988.

Knowles, J. et al., "Cellulase families and their genes," TIBTECH 5, pp. 255–261, 1987.

Luo, J., et al., "Detection of a Stable Intermediate in the Thermal Unfolding of a Cysteine–Free Form of Dihydrofolate Reductase from *Escherichia coli*" *Biochem.* vol. 34, No. 33, pp. 10669–10675, 1995.

Matthews, Brian W., "Structural and Genetic Analysis of Protein Stability," *Annu. Rev. Biochem.*, 62: 139–160. 1993.

(List continued on next page.)

*Primary Examiner*—Charles L. Patterson, Jr.
(74) *Attorney, Agent, or Firm*—Genencor International, Inc

(57) ABSTRACT

The present invention relates to variant EGIII cellulases that have improved stability and/or performance. The variant cellulases have replacements at sensitive residues to improve stability and/or performance.

11 Claims, 5 Drawing Sheets

OTHER PUBLICATIONS

Needleman, S., et al., "A General Method Applicable to the Search for Similarities in the Amino Acid Sequence of Two Proteins," *J. Mol. Biol.* vol. 48, pp. 443–453, 1970.

Ooi, Toshihiko, et al., "Cloning and sequence analysis of a cDNA for cellulase (Fl–CMCase) from Aspergillus aculeatus," *Curr. Genet.,* vol. 18, pp. 217–222, 1990.

Pace, C. Nick, "How to measure and predict the molar absorption coefficient of a protein," Protein Science, Cambridge University Press, 4:2411–2423, 1995.

Pearson, William R., et al., "Improved tools for biological sequence comparison," *Proc. Natl. Acad. Sci. USA,* vol. 85, pp. 2444–2448, Apr., 1988.

Protein Society, 14th Symposium, San Diego, CA, Aug. 5–9, 2000, pp. 111.

Russell, Rupert JM., et al., "Engineering thermostability: lessons from thermophilic proteins," *Curr. Opin. In Biotech.,* vol. 6, No. 4, pp. 370–374, 1995.

Saarilahti, Hannu T., et al., "CelS: a novel endoglucanase identified from *Erwinia carotovra* subsp. *carotovora*,sub. *cartovora,"* Gene, vol. 90, pp. 9–14, 1990.

Sakamoto, S., et al., "Cloning and sequencing of cellulase cDNA from Aspergillus kawachii and its expression in *Saccharomyces cerevisias*," *Curr..Genet.,* vol. 27, No. 5, pp. 435–439, 1995.

Sambrook, J. et al., *Molecular Cloning: A Laboratory Manual, 2$^{nd}$* ed., Cold Spring Harbor Laboratory Press, pp. 1.20–1.110,2.4–2.125,3.2–3.58,4.2–4.54, 16.2–16.81, 17.20–17.44.

Schulein, Martin, "Cellulases of *Trichoderma reesei*," *Methods in Enzymology,* 160, 25, pp. 234–242, 1988.

Sheir–Neiss, G., et al. "Characterization of the secreted cellulases of Trichoderma ressei wild type and mutants during controlled fermentations," Appl. Microbiol. Biotechnol., 20:46–53, 1984.

Smith, Temple F., et al., "Comparison of Biosequences," Adv. Appl. Math. 2:482–489, 1981.

Sulzenbacher, Gerlind, et al., "The Streptomyces lividans Family 12 Endoglucanase: Construction of the Catalytic Core, Exprssion, and X–ray Structure at 1.75 Å Resolution†‡," Biochemistry 36:16032–16039, 1997.

Sulzenbacher, Gerlind, et al., "The Crystal Structure of a 2–Fluorocellotriosyl Complex of the *Streptomyces lividans* Endoglucanase CelB2 at 1.2 Å Resolution†‡," *Biochem.* vol. 38, No. 15, pp. 4826–4833, 1999.

Tanner, J., et al., "Determinants of Enzyme Thermostability Observed in the Molecular Structure of *Thermus aquaticus* D–Glyceraldehyde–3–phosphate Dehydrogenase at 2.5 ÅResolution†‡," (1996) *Biochem.* vol. 35, No. 8, pp. 2597–2609, 1996.

Timberlake, William E., "Gene Cloning and Analysis," *More Gene Manipulations in Fungi,* Bennett & Lasure, ed., Academic Press, San Diego, pp. 70–76, 1991.

Watanabe, K. et al., "Multiple proline substitutions cumulatively thermostabilize *Bacillus cereus* ATCC7064 oligo–1, 6–glucosidase," *Eur. J. Biochem.,* vol. 226, pp. 277–283, 1994.

Zuber, H., "Temperature adaptation of lactate dehydrogenase, Structural, functional and genetic aspects," *Biophys. Chem.* 29:171–179, 1988.

Copy of USSN 09/321,981, Jones et al., filed May 28, 1999, our docket No. GC540–2, allowed application.

* cited by examiner

Figure 1: Amino Acid Sequence of Mature EGIII Protein

QTSCDQWATFTGNGYTVSNNLWGASAGSGFGCVTAVSLSGGASWHADWQWSGGQNNVKSY 60
QNSQIAIPQKRTVNSISSMPTTASWSYSGSNIRANVAYDLFTAANPNHVTYSGDYELMIW 120
LGKYGDIGPIGSSQGTVNVGGQSWTLYYGYNGAMQVYSFVAQTNTTNYSGDVKNFFNYLR 180
DNKGYNAAGQYVLSYQFGTEPFTGSGTLNVASWTASIN 218

FIGURE 2

DNA Sequence of EGIII Without Introns

ATGAAGTTCCTTCAAGTCCTCCCTGCCCTCATACCGGCCGCCCTGGCCCAAACCAGC
TGTGACCAGTGGGCAACCTTCACTGGCAACGGCTACACAGTCAGCAACAACCTTTGG
GGAGCATCAGCCGGCTCTGGATTTGGCTGCGTGACGGCGGTATCGCTCAGCGGCGGG
GCCTCCTGGCACGCAGACTGGCAGTGGTCCGGCGGCCAGAACAACGTCAAGTCGTAC
CAGAACTCTCAGATTGCCATTCCCCAGAAGAGGACCGTCAACAGCATCAGCAGCATG
CCCACCACTGCCAGCTGGAGCTACAGCGGGAGCAACATCCGCGCTAATGTTGCGTAT
GACTTGTTCACCGCAGCCAACCCGAATCATGTCACGTACTCGGGAGACTACGAACTC
ATGATCTGGCTTGGCAAATACGGCGATATTGGGCCGATTGGGTCCTCACAGGGAACA
GTCAACGTCGGTGGCCAGAGCTGGACGCTCTACTATGGCTACAACGGAGCCATGCAA
GTCTATTCCTTTGTGGCCCAGACCAACACTACCAACTACAGCGGAGATGTCAAGAAC
TTCTTCAATTATCTCCGAGACAATAAAGGATACAACGCTGCAGGCCAATATGTTCTT
AGCTACCAATTTGGTACCGAGCCCTTCACGGGCAGTGGAACTCTGAACGTCGCATCC
TGGACCGCATCTATCAAC

FIGURE 3A

```
                              1                                                          60
            T._reesei         M.........KF.LQVLPALIPAALAQTS...............CDQWATFTGNG..YTV
        H._schweinitzii       M.........KF.LQVLPAILPAALAQTS...............CDQYATFSGNG..YIV
         A._aculeatus__*      M.........KAFHL.LAALAGAAVAQQAQ..............LCDQYATYTGGV..YTI
          A._kawachii__*      M.........KLSMT.LSLFAATAMGQT................MCSQYDSASSPP..YSV
          A._kawachii_2       M.........KAFHL.LAALSGAAVAQQAQ..............LCDQYATYTGGV..YTI
           A._oryzae__*       M.........KLSLA.LATLVATAFSQE................LCAQYDSASSPP..YSV
             H._grisei        M........LKSALLLGAAAVSVQSASIPTIPANLEPRQIR.SLCELYGYWSGNG..YEL
          H._insolens__*      M........LKSALLLGPAAVSVQSASIPTIPANLEPRQIR.SLCELYGYWSGNG..YEL
     Chaetomium_brasiliense   M.........KLTLVLFVSSLA......AATPLGWRERQQQVSLCGQSSSWSGNG..YQL
            F._equseti        M.........KSTLLLAGAFAPLAFAKD................LCEQYGYLSSDG..YSL
           F._javanicum_1     M.........KSAIVA.ALAGLAAASPTRLIPRGQ........FCGQWDSETAGA..YTI
           F._javanicum_2     M.........K..FFGVVSASLAATAVATPTTPTETIEKRDTTWCDAFGSLATSG..YTV
           G._roseum_Rj_1     M.........KANIVILSLFAPLAAVAQT...............LCGQYSSNTQGG..YIF
           G._roseum_Rj_2     M.........KSIISFFGLATLVAAAPSQNPTRTQPLEKRATTLCGQWDSVETGG..YTI
           G._roseum_PA_3     M.........KFQLLSLTAFAPLSLAA.................LCGQYQSQSQGG..YIF
           G._roseum_Rj_4     M.........KTGIAYLAAVLPLA.MAES...............LCDQYAYLSRDG..YNF
       Memnoniella_echinata   M.........KVAAL.LVALSPLAF.AQS...............LCDQYSYYSSNG..YEF
       Emericella_desertoru   M.........K..LLALSLVSLASAASAASIL.SNTFTRRSD.FCGQWDTATVGN..FIV
         Actinomycete_11AG8   MRS......HPRS..ATM.TVLVVLASLGALLTAAAPAQANQQICDRYGTTTIQD.RYVV
         S._lividans_CelB__*  MRTLRPQARAPRGLLAALGAVLAAFALVSSLVTAAAPAQADTTICEPFGTTTIQG.RYVV
       Rhodothermus_marinus__*MNVMR..AVLVLSLLLLFGCDWL.FPDGDNGKEPEPEPEPTVELCGRWDARDVAGGRYRV
         Erwinia_carot___*    MQTVNTQPHRIFRVLLPAVFSSLLLSSLTVSAASSSNDADKLYF.........GNNKYYL 61                                                         120
            T._reesei         SNNLWGASAGSGF..GCV.TAVSLSGG.ASWHADWQWSGGQNNVKSYQNS..........
        H._schweinitzii       SNNLWGASAGSGF..GCV.TSVSLNGA.ASWHADWQWSGGQNNVKSYQNV..........
         A._aculeatus__*      NNNLWGKDAGSG..SQCTTVNSASSAG.TSWSTKWNWSGGENSVKSYANS..........
          A._kawachii__*      NQNLWGEYQGTG..SQCVYVDKLSSSG.ASWHTKWTWSGGEGTVKSYSNS..........
          A._kawachii_2       NNNLWGKDAGSG..SQCTTVNSASSAG.TSWSTKWNWSGGENSVKSYANS..........
           A._oryzae__*       NNNLWGQDSGTGFTSQCVYVDNLSSSG.AAWHTTWTWNGGEGSVKSYSNS..........
             H._grisei        LNNLWGKDTATS.GWQCTYLDGTNNGG.IQWSTAWEWQGAPDNVKSYPYV..........
          H._insolens__*      LNNLWGKDTATS.GWQCTYLDGTNNGG.IQWSTAWEWQGAPDNVKSYPYV..........
     Chaetomium_brasiliense   NNNLWGQSRATS.GSQCTYLDSSSNSG.IHWHTTWTWEGGEGEVKSYAYS..........
            F._equseti        NNNVWGKDSGTGD..QCTHVNWNNANG.AGWDVEWNWSGGKDNVKSYPNS..........
           F._javanicum_1     YNNLWGKDNAES.GEQCTTNSGEQSDGSIAWSVEWSWTGGQGQVKSYPNA..........
           F._javanicum_2     YHNNWGKGDATS.GSQCTTFTSVSNNNFV.WSTSWTWAGGAGKVKSYSNV..........
           G._roseum_Rj_1     NNNMWGMGSGSGS..QCTYVDKVWAEG.VAWHTDWSWSGGDNNVKSYPYS..........
           G._roseum_Rj_2     YNNLWGQDNG.S.GSQCLTVEGV.TDGLAAWSSTWSWSGGSSSVKSYSNA..........
           G._roseum_PA_3     NNNKWGQGSGSGS..QCLTIDKTWDSN.VAFHADWSWSGGTNNVKSYPNA..........
           G._roseum_Rj_4     NNNEWGAATGTGD..QCTYVDSTSSGG.VSWHSDWTWSGSESEIKSYPYS..........
       Memnoniella_echinata   NNNMWGRNSGQGN..QCTYVDYSSPNG.VGWRVNWNWSGGDNNVKSYPYS..........
       Emericella_desertoru   YNNLWGQDNADS.GSQ..TGVDSANGNSISWHTTWSWSGGSSSVKSYANA..........
         Actinomycete_11AG8   QNNRWGTSAT.....QCINVT..GNGFEITQADGS..VPTNGAPKSYPSVYDGCHYG...
         S._lividans_CelB__*  QNNRWGSTAP.....QCVTAT..DTGFRVTQADGS..APTNGAPKSYPSVFNGCHYT...
       Rhodothermus_marinus__*INNVWGAETA.....QCIEVGLETGNFTITRADHD..NGNNVA..AYPAIYFGCHWAPAR
         Erwinia_carot___*    FNNVWGKDEIKGWQQTIFYNSPISMG....WN..WHWPSSTHSVKAYPSLVSGWHWTAG.

121                                                        180
            T._reesei         .QIAIP.QKRTVNSISSMPTTASW...SYSGSNIRANVAYDL.FTAANPNHVTYSGDYEL
        H._schweinitzii       .QINIP.QKRTVNSIGSMPTTASW...SYSGSDIRANVAYDL.FTAANPNHVTYSGDYEL
         A._aculeatus__*      .GLTF..NKKLVSQISQIPTTARW.S..YDNTGIRADVAYDL.FTAADINHVTWSGDYEL
          A._kawachii__*      .GLTF..DKKLVSDVSSIPTSVTW.SQD..DTNVQADVSYDL.FTAANADHATSSGDYEL
          A._kawachii_2       .GLSF..NKKLVSQISHIPTAARW.S..YDNTCIRRGRAYDL.FTAADINHVTWSGDYEL
           A._oryzae__*       .AVTF..DKKLVSDVQSIPTDVEW.SQDFTNTNVNADVAYDL.FTAADQNHVTYSGDYEL
             H._grisei        .GKQIQRGRK.ISDINSMRTSVSW...TYDRTDIRANVAYDV.FTARDPDHPNWGGDYEL
          H._insolens__*      .GKQIQRGRK.ISDINSMRTSVSW...TYDRTDIRANVAYDV.FTARDPDHPNWGGDYEL
     Chaetomium_brasiliense   .GRQVSTGLT.IASIDSMQTSVSW...EYNTTDIQANVAYDI.FTAEDPDHEHSSGDYEL
            F._equseti        .ALLIGEDKKTISSITNMQSTAEW...KYSGDNLRADVAYDL.FTAADPNHETSSGEYEL
           F._javanicum_1     .VVEI..EKKTLGEVSSIPSA..W.DWTYTGNGIIANVAYDL.FTSSTESGDA...EYEF
           F._javanicum_2     .ALEK..INKKISDIKSVSTR...W.IWRYTGTKMIANVSYDL.WFAPTASSNN...AYEI
           G._roseum_Rj_1     .GRELGT.KRIVSSIKSISSGADW...DYTGSNLRANAAYDI.FTSANPNHATSSGDYEV
           G._roseum_Rj_2     .VLSA..EAARISAISSIPSK..W.EWSYTGTDIVANVAYDL.FSNTDCGDTP...EYEI
           G._roseum_PA_3     .GLEFSR.GKKVSSIGTINGGADW...DYSGSNIRANVAYDI.FTSADPNHVTSSGDYEL
           G._roseum_Rj_4     .GLDLPE..KKIVTSIGSISTGAEW...SYSGSDIRADVAYDT.FTAADPNHATSSGDYEV
       Memnoniella_echinata   .GRQLPT..KRIVSWIGSLPTTVSW...NYQGNNLRANVAYDL.FTAANPNHPNSSGDYEL
       Emericella_desertoru   .AYQF..TSTKLNSLSSIPTS..W.KWQYSTTDIVANVAYDL.FTSSSAGGDS...EYEI
         Actinomycete_11AG8   ...NCAPRTTLPMRISSIGSAPSSVSYRYTGNGVY.NAAYDIWLDPTPRTNGVNR..TEI
         S._lividans_CelB__*  ...NCSPGTDLPVRLDTVSAAPSSISYGFVDGAVY.NASYDIWLDPTARTDGVNQ..TEI
       Rhodothermus_marinus__*AIRDCAARAGAVRRAHELDVTP.......ITTGRW.NAAYDIWFSPVTNSGNGYSGGAEL
         Erwinia_carot___*    ....YTENSGLPIQLSSNKSITSNVTYSIKATGTY.NAAYDIWFHTTDKANWDSSPTDEL 181                                                        240
            T._reesei         MIWLGKYGDIGPIGSS....QGTVNVGGQSWTLYYGYNGAMQV......YSFVAQT.NTT
        H._schweinitzii       MIWLGKYGDIGPIGSS....QGTVNVGGQTWTLYYGYNGAMQV......YSFVAQS.NTT
```

FIGURE 3B

```
         A._aculeatus__*  MIWLARYGGVQPIGSQ....IATATVDGQTWELWYG......ANGSQKTYSFVAPT.PIT
          A._kawachii__*  MIWLARYGSVQPIGKQ....IATATVGGKSWEVW..YGTSTQAGAEQKTYSFVAGS.PIN
          A._kawachii_2   MIWLARYGGVQPLGSQ.....IATATVEGQTWELWYG......VNGAQKTYSFVAAN.PIT
            A._oryzae__*  MIWLARYGTIQPIGTQ....IDTATVEGHTWELWFTYGTTIQAGAEQKTYSFVSAT.PIN
              H._grisei   MIWLARYGGIYPIGTF....HSQVNLAGRTWDLWTGYNGNMRV......YSFLPPSGDIR
          H._insolens__*  MIWLARYGGIYPIGTF....HSQVNLAGRTWDLWTGYNGNMRV......YSFLPPSGDIR
  Chaetomium_brasiliense  MIWLARYNNVSPIGSS....VATATVGGDTWDLFAGANGDMEV......YSFVAENT.MN
              F._equseti  MVWLARIGGVQPIGSL....QTSVTIEGHTWELWVGMNGSMKV......FSFVAPT.PVN
           F._javanicum_1 MIWLSALGGAGPISNDGSP.VATAELAGTSWKLYQGKNNQMTV......FSFVAESDV.N
           F._javanicum_2 MIWVGAYGGALPISTPGKGVIDRPTLAGIPWDVYKGPNGDVTV......ISFVASSNQ.G
            G._roseum_Rj_1 MIWLANLGGLTPIGSP....IGTVKAAGRDWELWDGYNGAMRV......YSFVAPS.QLN
            G._roseum_Rj_2 MIWLSALGGAGPISSTGSS.IATVTIAGASWNLWQGQNNQMAV......FSFVAESDQ.K
            G._roseum_PA_3 MIWLGKLGDIYPIGNS....IGRVKAANREWDLHVGYNGAMKV......FSFVAPS.PVT
            G._roseum_Rj_4 MIWLANLGGLTPIGSP....IGTVKAAGRDWELWDGYNGAMRV......YSFVAPS.QLN
     Memnoniella_echinata MIWLGRLGNVYPIGNQ....VATVNIAGQQWNLYYGYNGAMQV......YSFVSPN.QLN
      Emericella_desertoru MIWLAALGGAGPISSTGSS.IATVTLGGVTWSLYSGPNGSMQV......YSFVASSTT.E
         Actinomycete_11AG8 MIWFNRVGPVQPIGSP....VGTAHVGGRSWEVWTGSNGSNDVI......SFLAPSA.IS
          S._lividans_CelB_* MIWFNRVGPIQPIGSP....VGTASVGGRTWEVWSGGNGSNDVL......SFVAPSA.IS
         Rhodothermus_marinus_* MIWLNWNGGVMPGGSR....VATVELAGATWEVWYADWDWNYIA......YRRTTPT.TS
            Erwinia_carot___* MIWLNDTNA.....GPAGDYIETVFLGDSSWNVFKGWINADN.GGGWNVFSFVHTSGTNS 241                                                        300
              T._reesei   NYSGDVKNFFNYLRDNKGYNAAGQYV..LSYQFGTEPF..TGSGT.LNVASWTASI.N..
         H._schweinitzii  SYSGDVKNFFNYLRDNKGYNAGGQYV..LSYQFGTEPF..TGSGT.LNVASWTASI.N..
         A._aculeatus__*  SFQGDVNDFFKYLTQNHGFPASSQYLI..TLQFGTEPF..TGGPATLSVSNWSASVQQAG
          A._kawachii__*  SWSGDIKDFFNYLTQNQGFPASSQHLI..TLQCGTEPF..TGGPATFTVDNWTASVN...
          A._kawachii_2   SFQGDINDFFKYLTQNHGFPASSQYLIILALQFGTEPF..TGGPATLNVADWSASVQ...
            A._oryzae__*  TFGGDIKKFFDYITSKHSFPASAQYLI..NMQFGTEPFFTTGGPVTFTVPNWTASVN...
              H._grisei   DFSCDIKDFFNYLERNHGYPAREQNLIV..YQVGTECF..TGGPARFTCRDFRADL....
          H._insolens__*  DFSCDIKDFFNYLERNHGYPAREQNLIV..YQVGTECF..TGGPARFTCRDFRADL....
  Chaetomium_brasiliense  SFSGDVKDFFDYLEQNVGFPVDDQYLLV..FELGSEAF..TGGPATLSVSQFSANI....
              F._equseti  NFNADIKQFWDYLTKSQNFPADNQYL..LTFQFGTEPF..TGDNAKFTVTNFNAHLK...
           F._javanicum_1 NFCGDLADFTDYLVDNHGVSSSQ...ILQSVGAGTEPF..EGTNAVFTTNNYHADVE...
           F._javanicum_2 NFQADLKEFLNYLTSKQGLPSNY...VATSFQAGTEPF..EGTNAVLKTSAYTISVN...
            G._roseum_Rj_1 SFDGEIMDFFYVVKDMRGFPADSQHL..LTVQFGTEPI..SGSGAKFSVSHWSAKLG...
            G._roseum_Rj_2 SFSGDLNDFIQYLVDSQGYSGSQ...CLYSIGAGTEPF..TGTDAEFITTGYSVSVSAGD
            G._roseum_PA_3 RFDGNIMDFFYVMRDMQGYPMDKQYL..LSLQFGTEPF..TGSNAKFSCWYFGAKIK...
            G._roseum_Rj_4 SFDGEIMDFFYVVKDMRGFPADSQHL..LTVQFGTEPI..SGSGAKFSVSHWSAKLG...
     Memnoniella_echinata YFSGNVKDFFTYLQYNRAYPADSQYL..ITYQFGTEPF..TGQNAVFTVSNWSAQQNN..
      Emericella_desertoru SFSADLMDFINYLAENQGLSSSQ...YLTHVQAGTEPF..TGTDATLTVSSYSVSVS...
         Actinomycete_11AG8 SWSFDVKDFVD.QAVSHGLATPDWYLT..SIQAGFEPW...EGGTGLAVNSFSSAVNAG.
          S._lividans_CelB_* GWSFDVMDFVR.ATVARGLAENDWYLT..SVQAGFEPW...QNGAGLAVNSFSSTVETGT
         Rhodothermus_marinus_* VSELDLKAFID.DAVARGYIRPEWYLH..AVETGFELW...EGGAGLRTADFSVTVQ...
            Erwinia_carot___* A.SLNIRHFTDYLVQTKQWMSDEKYIS..SVEFGTEIF...GGDGQIDITEWRVDVK...

301                                                        360
              T._reesei   ............................................................
         H._schweinitzii  ............................................................
         A._aculeatus__*  F...........................EPWQNGAGLAVNSF....
          A._kawachii__*  ............................................................
          A._kawachii_2   ............................................................
            A._oryzae__*  ............................................................
              H._grisei   ....................................W.......
          H._insolens__*  ....................................W.......
  Chaetomium_brasiliense  .....................................A......
              F._equseti  ............................................................
           F._javanicum_1 ............................................................
           F._javanicum_2 ............................................................
            G._roseum_Rj_1 ............................................................
            G._roseum_Rj_2 SGCDETTTSSQAQSSTVETSTATQPQS...SSTVVPTVTLS.QPSNESTTTPVQSQ....
            G._roseum_PA_3 ............................................................
            G._roseum_Rj_4 ............................................................
     Memnoniella_echinata ............................................................
      Emericella_desertoru ............................................................
         Actinomycete_11AG8 ..GGNGGTPGTPAACQVSYSTHTWPGGFTVDTTITNTGSTPVDGWELDFTLPAGHTVTSA
          S._lividans_CelB_* PGGTDPGDPGGPSACAVSYGTNVWQDGFTADVTVTNTGTAPVDGWQLAFTLPSGQRITNA
         Rhodothermus_marinus_* ............................................................
            Erwinia_carot___* ............................................................

```
419
              T._reesei        ..............................................................
         H._schweinitzii       ..............................................................
         A._aculeatus__*       ......SSTV....................................................
          A._kawachii__*       ..............................................................
          A._kawachii_2        ..............................................................
            A._oryzae__*       ..............................................................
               H._grisei       ..............................................................
           H._insolens__*      ..............................................................
   Chaetomium_brasiliense      ..............................................................
               F._equseti      ..............................................................
          F._javanicum_1       .............................................................Y
          F._javanicum_2       ..............................................................
           G._roseum_Rj_1      ..............................................................
           G._roseum_Rj_2      ......PSSVETTPTAQPQSSSVQTTTTAQA....QPTSGTGCSRRRKRR......AVV
           G._roseum_PA_3      ..............................................................
           G._roseum_Rj_4      ..............................................................
      Memnoniella_echinata     ..............................................................
       Emericella_desertoru    ..............................................................
         Actinomycete_11AG8    WNALISPASGAVTARSTGSNGRIAANGGTQSFGFQGTSSGTGFNAPAGGRLNGTSCTVR
         S._lividans_CelB__*   WNASLTPSSGSVTATGASHNARIAP.GGSLSFGFQGTYGGA.FAEPTGFRLNGTACTTV
     Rhodothermus_marinus__*   ..............................................................
           Erwinia_carot___*   ..............................................................
```

MUTANT EGIII CELLULASE, DNA ENCODING SUCH EGIII COMPOSITIONS AND METHODS FOR OBTAINING SAME

CROSS-REFERENCE TO RELATED APPLICATIONS

This Application is related to but does not claim priority to concurrently filed applications with attorney docket numbers GC546C1, GC630, GC631 and GC555C1, filed on Aug. 4, 2000, all of which are incorporated by reference in their entirety.

GOVERNMENT SPONSORED RESEARCH AND DEVELOPMENT

Not Applicable.

BACKGROUND OF THE INVENTION

Cellulases are enzymes that are capable of hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al., (1987), TIBTECH 5, 255–261); and are known to be produced by a large number of bacteria, yeasts and fingi.

Although cellulases are used to degrade wood pulp and animal feed, cellulases are primarily used in the treatment of textiles, e.g., in detergent compositions for assisting in the removal of dirt or grayish cast (see e.g., Great Britain Application Nos. 2,075,028, 2,095,275 and 2,094,826) or in the treatment of textiles prior to sale to improve the feel and appearance of the textile. Thus, Great Britain Application No. 1,358,599 illustrates the use of cellulase in detergents to reduce the harshness of cotton containing fabrics.

Cellulases have also been used in the treatment of textiles to recondition used fabrics by making their colors more vibrant (see e.g., *The Shizuoka Prefectural Hammamatsu Textile Industrial Research Institute Report* 24:54–61 (1986)). Repeated washing of cotton containing fabrics results in a grayish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Because of its effectiveness in many industrial processes, there has been a trend in the field to search for specific cellulase compositions or components that have particularly effective performance profiles with respect to one or more specific applications. As possible sources of cellulases, practitioners have focused on fuigi and bacteria. For example, cellulase produced by certain fungi such as Trichoderma spp. (especially *Trichoderma reesei*) have been given much attention because a complete cellulase system capable of degrading crystalline forms of cellulose is readily produced in large quantities via fermentation procedures. This specific cellulase complex has been extensively analyzed to determine the nature of its specific components and the ability of those components to perform in industrial processes (see, Wood et al., "Methods in Enzymology", 160, 25, pages 234, et seq. (1988). U.S. Pat. No. 5,475,101 (Ward et al.) discloses the purification and molecular cloning of one particularly useful enzyme called endoglucanase III (EGIII) which is derived from *Trichoderma reesei*.

PCT Publication No. WO 94/14953 discloses endoglucanases that are encoded by a nucleic acid which comprises any one of a series of DNA sequences, each having 20 nucleotides.

Ooi, et al., *Curr. Genet.* 18:217–222 (1990) disclose the cDNA sequence coding for endoglucanase F1-CMC produced by *Aspergillus aculeatus* that contains the amino acid strings NNLWG, ELMIW and GTEPFT. Sakamoto, et al., *Curr. Genet.* 27:435–439 (1995) discloses the cDNA sequence encoding the endoglucanase CMCase-1 From *Aspergillus kawachii* IFO 4308 which contains the amino acid strings ELMIW and GTEPFT. Ward, et al., discloses the sequence of EGIII having the amino acid strings NNLWG, ELMIW and GTEPFT. Additionally, two cellulase sequences, one from *Erwinia carotovara* and *Rhodothermus marinus* are disclosed in Saarilahti, et al., Gene 90:9–14 (1990) and Hreggvidsson, et al., *Appl. Environ. Microb.* 62:3047–3049 (1996) that contain the amino acid string ELMIW.

Despite knowledge in the art related to many cellulase compositions having applications in some or all of the above areas, there is a continued need for new cellulase compositions which have improved stability under conditions present in applications for which cellulases are useful, e.g., household and laundry detergents and textile treatment compositions.

SUMMARY OF THE INVENTION

A variant EGIII cellulase is provided, wherein the cellulase comprises a substitution at a residue that is sensitive to temperature stress and wherein the variant EGIII cellulase is derived from *T. reesei* EGIII cellulase. In a preferred embodiment, the variant comprises a substitution or deletion at a position corresponding to one or more residues W7, G31, A35, H45, S63, S77, M79, H108, T145, Y147, M154, Q162, T163, N167, N174, and/or V192 in EGIII. In a more preferred embodiment, the variant comprises a substitution at a position corresponding to one or more of residues W7Y, G31Q, A35V, H45Q, S63V, S77G, M79I, H108R, T145E, Y147W, M154N, Q162P, T163S, N167S, N174D and/or V192L.

In an alternative embodiment of this invention, a DNA that encodes a variant EGIII cellulase is provided. In a preferred embodiment, the DNA is in a vector. In another aspect of this embodiment the vector is used to transfect a host cell.

In yet another embodiment, a method of producing a variant EGIII cellulase having improved stability and/or performance is provided. The method comprises the steps of culturing the host cell in a suitable culture medium under suitable conditions to produce cellulase and obtaining said produced cellulase. In still another embodiment, a detergent composition comprising a surfactant and a variant EGIII cellulase is provided, wherein the cellulase comprises a variant EGIII cellulase comprising a substitution at residue sensitive to temperature. In a preferred embodiment, the variant EGIII cellulase comprises a substitution or deletion at a position corresponding to one or more residues W7, G31, A35, H45, S63, S77, M79, H108, T145, Y147, M154, Q162, T163, N167, N174, and/or V192in EGIII. In a most preferred embodiment, the variant EGIII cellulase comprises a substitution at a position corresponding to one or more of residues at position W7Y, G31Q, A35V, H45Q, S63V, S77G, M79I, H108R, T145E, Y147W, M154N, Q162P, T163S, N167S, N174D and/or V192L.

In another embodiment the variant EGIII cellulase of this invention is used in the treatment of a cellulose-containing textile, in particular in ston washing indigo dyed denim. In other aspects of this embodiment, the cellulase of this invention is used as a feed additive, in the treatment of wood pulp, and in the reduction of biomass to glucose.

BRIEF DESCRIPTION OF THE DRAWINGS

FIG. 1 illustrates the amino acid sequence of EGIII from *Trichoderma reesei*. (SEQ ID NO:31)

FIG. 2 illustrates the DNA sequence of EGIII from *Trichoderma reesei* without introns. (SEQ ID NO:32)

FIG. 3 illustrates an alignment of the full length sequence of 20 EGIII-like cellulases in alignment with EGIII, indicating equivalent residues based on primary sequence modeling, including those derived from *Trichoderma reesei*, (SEQ ID NO:33) *Hypocrea schweinitzii*, (SEQ ID NO:34) *Aspergillus aculeatus*, (SEQ ID NO:35) *Aspergillus kawachii*, (1), (SEQ ID NO:36) *Aspergillus kawachii*, (2), (SEQ ID NO:37) *Aspergillus oryzae*, (SEQ ID NO:38) *Humicola grisea*, (SEQ ID NO:39) *Humicola insolens*, (SEQ ID NO:40) *Chaetomium brasilliense*, (SEQ ID NO:41) *Fusarium equiseti*, (SEQ ID NO:42) *Fusarium javanicum*, (1), (SEQ ID NO:43) *Fusarium javanicum*, (2), (SEQ ID NO:44) *Gliocladium roseum*, (1), (SEQ ID NO:45) *Gliocladium roseum*, (2), (SEQ ID NO:46) *Gliocladium roseum*, (3), (SEQ ID NO:47) *Gliocladium roseum*, (4), (SEQ ID NO:48) *Memnoniella echinata*, (SEQ ID NO:49) *Emericella desertoru*, (SEQ ID NO:50) *Alctinomycete* 11AG8, (SEQ ID NO:51) *Streptomyces lividans CelB*, (SEQ ID NO:52) *Rhodothermus marinus*, (SEQ ID NO:53) and *Erwinia carotovara*, (SEQ ID NO:54).

DETAILED DESCRIPTION OF THE INVENTION

The Applicants earlier isolated a novel cellulase from *Streptomyces lividans* (see, U.S. patent application Ser. No. 09/104,308, filled Jun. 24, 1998 and U.S. patent application filed May 28, 1999, and given GCI Docket Number GC540-2, both of which are incorporated by reference in their entirety) which has significant homology to EGIII from *Trichoderma reesei*. Analysis of this cellulase has resulted in the discovery that substantial differences exist in terms of performance between the two cellulases, despite the significant homology. In fact, the homologous enzyme has significantly increased performance under conditions of thermal stress or in the presence of surfactants. This indicates the positions of non-homology lie in portions or areas of the protein that have a significant impact on the stability and/or performance of EGIII. Thus, Applicants discovered that by optimizing residues in EGIII at one or more of the different positions by recruiting residues from 11AG8, it is possible to optimize the performance of EGIII.

Accordingly, the present invention relates to a variant EGIII cellulase having improved performance in the presence of, e.g., surfactant and/or thermal mediated stress. The variant is characterized by replacement of one or more residues identified herein as being critical for stability and/or performance with a residue that confers improved stability and/or performance to the enzyme. Preferably, but not necessarily, the sensitive residue is replaced with a residue which has improved oxidative, alkaline or thermal stability compared to the wild type (*T. reesei* EGIII) residue at that position and is present in *Streptomyces lividans* 11AG8. Suitable substitutions may be any substitution that modifies stability, particularly preferred substitutions being those which provide improved stability and most preferred substitutions being those which provide conservative modifications in terms of charge, polarity and/or size. As a non-limiting example, substitutions which are particularly of value include substitutions wherein leucine is modified to an isoleucine, isoleucine is modified to a leucine, tryptophan is modified to a tyrosine, threonine is modified to an asparagine, alanine is modified to a glycine, serine is modified to an asparagine, glycine is modified to a proline and asparagine is modified to a threonine.

Definitions

Within the specification, certain terms are disclosed which are defined below so as to clarify the nature of the claimed invention.

"Cellulase" is a well-classified category of enzymes in the art and includes enzymes capable of hydrolyzing cellulose polymers to shorter cello-oligosaccharide oligomers, cellobiose and/or glucose. Common examples of cellulase enzymes include exo-cellobiohydrolases and endoglucanases and are obtainable from many species of cellulolytic organisms, particularly including fumgi and bacteria.

"EGIII cellulase" refers to the endoglucanase component described in U.S. Pat. No. 5,475,101 and *Proceedings on the Second TRICEL Symposium on Trichoderma reesei Cellulases And Other Hydrolases*, Suominen & Reinikainen eds., Espoo Finland (1993), pp. 153–158 (Foundation for Biotechnical and Industrial Fermentation Research, Vol. 8). As discussed therein, EGIII is derived from *Trichoderma reesei* and is characterized by a pH optimum of about 5.8, an isoelectric point (pI) of about 7.4 and a molecular weight of about 25 kD. The enzyme commonly referred to as EGII from *Trichoderma reesei* has been previously referred to in the literature by the nomenclature EGIII by some authors, but that enzyme differs substantially from the enzyme defined herein as EGIII in terms of molecular weight, pI and pH optimum.

"Cellulose containing fabric" means any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g., lyocell). Specifically included within the definition of cellulose containing fabric is any yarn or fiber made of such materials. Cellulose containing materials are often incorporated into blends with materials such as synthetic fibers and natural non-cellulosic fibers such as wool and silk.

A residue in an EGIII homolog from *S. lividens* which is "corresponding" or "equivalent" to a residue present in EGIII means a residue which exists in an equivalent position to that in EGIII, as indicated by primary sequence homology, tertiary structural homology (as shown by, e.g., crystal structure or computer modeling) or functional equivalence.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of a EGIII homolog from *S. lividens* and *T. reesei* EGIII (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the EGIII homolog in question to the *T. reesei* EGIII. The best model is the crystallographic model giving the lowest R factor for experimental diffraction data at the highest resolution available.

$$R\ factor = \frac{\sum_h |Fo(h)| - |Fc(h)|}{\sum_h |Fo(h)|}$$

Equivalent residues which are functionally analogous to a specific residue of *T. reesei* EGIII are defined as those amino acids of a cellulase which may adopt a conformation such that they either alter, modify or contribute to protein structure, substrate binding or catalysis in a manner defined and attributed to a specific residue of the *T. reesei* EGIII. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *T. reesei* EGIII. The coordinates of the three dimensional structure of *T. reesei* EGIII can be used as outlined above to determine equivalent residues on the level of tertiary structure. The crystal structure of *T. reesei* EGIII is presented The Protein Society, Fourteenth Symposium. San Diego, Calif. Aug. 5–9, 2000, the disclosure of which is incorporated by reference in its entirety. The coordinates of CelB of *Streptomyces lividans*, a homologous member of the Family 12 glycosyl hydrolases is provided in Sulzenbacher, et al., *Biochemistry* 36:6032 (1997) and in Sulzenbacher, et al., *Biochemistry* 38:4826 (1999).

"Cotton-containing fabric" means sewn or unsewn fabrics, yarns or fibers made of pure cotton or cotton blends including cotton woven fabrics, cotton knits, cotton denims, cotton yarns, raw cotton and the like. When cotton blends are employed, the amount of cotton in the fabric is preferably at least about 35 percent by weight cotton. When employed as blends, the companion material employed in the fabric can include one or more non-cotton fibers including cellulosic or synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Detergent composition" means a mixture that is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers. Such compositions are generally used for cleaning soiled garments and are not used during the manufacturing process, in contrast to stonewashing compositions. Detergent compositions comprising cellulase are described in, for example, U.S. Pat. No. 5,290,474 and EP Publication No. 271 004, incorporated herein by reference.

"DNA vector" means a nucleotide sequence that comprises one or more DNA fragments or DNA variant fragments encoding an EGIII or variants described above, which can be used, upon transformation into an appropriate host cell, to cause expression of the EGIII.

"Expression vector" means a DNA construct comprising a DNA sequence that is operably linked to a suitable control sequence capable of effecting the expression of the DNA in a suitable host. Such control sequences may include a promoter to effect transcription, an optional operator sequence to control transcription, a sequence encoding suitable ribosome-binding sites on the mRNA, and sequences that control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* (*reesei*) is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors that serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage $\lambda$, e.g., NM989, and other DNA phages, e.g., M13 and filamentous single stranded DNA phages, yeast plasmids such as the $2\mu$ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook, et al., *Molecular Cloning: A Laboratory Manual, Second Edition*, Cold Spring Harbor Press (1989). Often, such expression vectors including the DNA sequences of the invention are transformed into a unicellular host by direct insertion into the genome of a particular species through an integration event (see e.g., Bennett & Lasure, More Gene Manipulations in Fungi, Academic Press, San Diego, pp. 70–76 (1991) and articles cited therein describing targeted genomic insertion in fungal hosts, incorporated herein by reference).

"Functionally attached to" means that a regulatory region, such as a promoter, terminator, secretion signal or enhancer region is attached to a structural gene and controls the expression of that gene.

"Host strain" or "host cell" means a suitable host for an expression vector comprising DNA according to the present invention. Host cells useful in the present invention are generally procaryotic or eucaryotic hosts, including any transformable microorganism in which expression can be achieved. Specifically, host strains may be *Bacillus subtilis, Escherichia coli, Trichoderma reesei* (*reesei*), *Saccharomyces cerevisiae* or *Aspergillus niger*. Host cells are transformed or transfected with vectors constructed using recombinant DNA techniques. Such transformed host cells are capable of both replicating vectors encoding swollenin and its variants (mutants) or expressing the desired peptide product. In a preferred embodiment according to the present invention, "host cell" means both the cells and protoplasts created from the cells of Trichoderma sp.

"Stonewashing" means the treatment of cellulose containing fabric with a cellulase solution under agitating and cascading conditions, e.g., in a rotary drum washing machine, to impart a "stonewashed" appearance to the denim. The cellulase solution according to the instant invention will functionally replace the use of stones in such art-recognized methods, either completely or partially. Methods for imparting a stonewashed appearance to denim are described in U.S. Pat. No. 4,832,864, which is incorporated herein by reference in its entirety. Generally, stonewashing techniques have been applied to indigo dyed cotton denim.

"Stonewashing composition" means a formulation for use in stonewashing cellulose containing fabrics. Stonewashing compositions are used to modify cellulose-containing fabrics prior to presentation for consumer sale, i.e., during the manufacturing process. In contrast, detergent compositions are intended for the cleaning of soiled garments.

"Signal sequence" means a sequence of amino acids bound to the N-terminal portion of a protein that facilitates the secretion of the mature form of the protein outside of the cell. This definition of a signal sequence is a functional one. The mature form of the extracellular protein lacks the signal sequence which is cleaved off during the secretion process.

"Surfactant" means any compound generally recognized in the art as having surface-active qualities. Thus, for example, surfactants comprise anionic, cationic and nonionic surfactants such as those commonly found in detergents. Cationic surfactants and long-chain fatty acid salts include saturated or unsaturated fatty acid salts, alkyl or alkenyl ether carboxylic acid salts, α-sulfofatty acid salts or esters, amino acid-type surfactants, phosphate ester surfactants, quaternary ammonium salts including those having 3 to 4 alkyl substituents and up to 1 phenyl substituted alkyl substituents. Examples of cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesul-fonates. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like. Examples of surfactants for use in this invention are disclosed in British Patent Application No. 2 094 826 A, the disclosure of which is incorporated herein by reference. Mixtures of such surfactants can also be used.

"Variant" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or, at one or more sites in the amino acid sequence, or insertion of one or more amino acids at one or more sites in the amino acid sequence. The preparation of an enzyme variant is preferably achieved by modifying a DNA sequence which encodes for the native protein, transformation of that DNA sequence into a suitable host, and expression of the modified DNA sequence to form the variant enzyme. The variant of the invention includes peptides comprising altered amino acid sequences in comparison with a precursor enzyme amino acid sequence (e.g., a wild type or native state enzyme), which peptides retain a characteristic enzyme nature of the precursor enzyme but which have altered properties in some specific aspect. For example, an EGIII variant may have an increased pH optimum or increased temperature or oxidative stability but will retain cellulolytic activity. It is acontemplated that variants according to the present invention may be derived from a DNA fragment encoding a cellulase derivative wherein the functional activity of the expressed cellulase derivative is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained.

Alignment of Amino Acid Sequences

The variant EGIIIs of this invention have amino acid sequences that are derived from the amino acid sequence of a precursor EGIII. The amino acid sequence of the EGIII variant differs from the precursor EGIII amino acid sequence by the substitution, deletion or insertion of one or more amino acids of the precursor amino acid sequence. In a preferred embodiment, the precursor EGIII is *Trichoderma reesei* EGIII. The mature amino acid sequence of *T. reesei* EGIII is shown in FIG. 1. (SEQ ID NO:31). Thus, this invention is directed to EGIII variants which contain amino acid residues at positions which are equivalent to the particular identified residue in *T. reesei* EGIII as well as at least one residue that is equivalent to an identified residue in *S. lividens* EGIII homolog. A residue (amino acid) of an EGIII homolog is equivalent to a residue of *Trichoderma reesei* EGIII if it is either homologous (i.e., corresponding in position in either primary or tertiary structure) or is functionally analogous to a specific residue or portion of that residue in *Trichoderma reesei* EGIII (i.e., having the same or similar functional capacity to combine, react, or interact chemically or structurally). As used herein, numbering is intended to correspond to that of the mature EGIII amino acid sequence as illustrated in FIG. 2 (SEQ ID NO:32). In addition to locations within the precursor EGIII, specific residues in the precursor EGIII corresponding to the amino acid positions that are responsible for instability when the precursor EGIII is under thermal or surfactant stress are identified herein for substitution or deletion. The amino acid position number (e.g., +51) refers to the number assigned to the mature *Trichoderma reesei* EGIII sequence presented in FIG. 1 (SEQ ID NO:31).

The precursor EGIIs of this invention include naturally occurring cellulases and recombinant cellulases (as defined herein). It is intended the DNA that encodes the precursor EGIII is modified rather than manipulation of the precursor cellulase enzyme per se. Suitable methods for such manipulation of the precursor DNA sequence include methods disclosed herein and in commonly owned U.S. Pat. Nos. 4,760,025 and 5,185,258.

Alignment of amino acid sequences to determine homology is preferably determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'–4, and a comparison of both strands.

The BLAST algorithm then performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

Additional specific strategies for modifying stability of EGIII cellulases are provided below:

(1) Decreasing the entropy of main-chain unfolding may introduce stability to the enzyme. For example, the introduction of proline residues may significantly stabilize the protein by decreasing the entropy of the unfolding (see, e.g., Watanabe, et al, *Eur. J. Biochem.* 226:277–283 (1994)). Similarly, glycine residues have no β-carbon, and thus have considerably greater backbone conformational freedom than many other residues. . Replacement of glycines, preferably with alanines, may reduce the entropy of unfolding and improve stability (see, e.g., Matthews, et al., *Proc. Natl. Acad. Sci. USA* 84; 6663–6667 (1987)). Additionally, by shortening external loops it may be possible to improve stability. It has been observed that hyperthermophile produced proteins have shorter external loops than their mesophilic homologues (see, e.g., Russel, et al., *Current Opinion's in Biotechnology* 6:370–374 (1995)). The introduction of disulfide bonds may also be effective to stabilize distinct tertiary structures in relation to each other. Thus, the introduction of cysteines at residues accessible to existing cysteines or the introduction of pairs of cysteines that could form disulfide bonds would alter the stability of an EGIII variant.

(2) Decreasing internal cavities by increasing side-chain hydrophobicity may alter the stability of an enzyme. Reducing the number and volume of internal cavities increases the stability of enzyme by maximizing hydrophobic interactions and reducing packing defects (see, e.g., Matthews, *Ann. Rev. Biochem.* 62:139–160 (1993); Burley, et al., *Science* 229:23–29 (1985); Zuber, *Biophys. Chem.* 29:171–179 (1988); Kellis, et al., *Nature* 333:784–786 (1988)). It is known that multimeric proteins from thermophiles often have more hydrophobic sub-unit interfaces with greater surface complementarity than their mesophilic counterparts (Russel, et al., supra). This principle is believed to be applicable to domain interfaces of monomeric proteins. Specific substitutions that may improve stability by increasing hydrophobicity include lysine to arginine, serine to alanine and threonine to alanine (Russel, et al., supra). Modification by substitution to alanine or proline may increase side-chain size with resultant reduction in cavities, better packing and increased hydrophobicity. Substitutions to reduce the size of the cavity, increase hydrophobicity and improve the complementarity the interfaces between the domains of EGIII may improve stability of the enzyme. Specifically, modification of the specific residue at these positions with a different residue selected from any of phenylalanine, tryptophan, tyrosine, leucine and isoleucine may improve performance.

(3) Balancing charge in rigid secondary structure, i.e., α-helices and β-turns may improve stability. For example, neutralizing partial positive charges on a helix N-terminus with negative charge on aspartic acid may improve stability of the structure (see, e.g., Eriksson, et al., *Science* 255:178–183 (1992)). Similarly, neutralizing partial negative charges on helix C-termninus with positive charge may improve stability. Removing positive charge from interacting with peptide N-terminus in β-turns should be effective in conferring tertiary structure stability. Substitution with a non-positively charged residue could remove an unfavorable positive charge from interacting with an amide nitrogen present in a turn.

(4) Introducing salt bridges and hydrogen bonds to stabilize tertiary structures may be effective. For example, ion pair interactions, e.g., between aspartic acid or glutamic acid and lysine, arginine or histidine, may introduce strong stabilizing effects and may be used to attach different tertiary structure elements with a resultant improvement in thermostability. Additionally, increases in the number of charged residue/non-charged residue hydrogen bonds, and the number of hydrogen-bonds generally, may improve thermostability (see, e.g., Tanner, et al., *Biochemistry* 35:2597–2609). Substitution with aspartic acid, asparagine, glutamic acid or glutamine may introduce a hydrogen bond with a backbone amide. Substitution with arginine may improve a salt bridge and introduce an H-bond into a backbone carbonyl.

(5) Avoiding thermolabile residues in general may increase thermal stability. For example, asparagine and glutamine are susceptible to deamidation and cysteine is susceptible to oxidation at high temperatures. Reducing the number of these residues in sensitive positions may result in improved thermostability (Russel, et al., supra). Substitution or deletion by any residue other than glutamine or cysteine may increase stability by avoidance of a thermolabile residue.

(6) Stabilization or destabilization of binding of a ligand that confers modified stability to EGIII variants. For example, a component of the matrix in which the EGIII variants of this invention are used may bind to a specific surfactant/ thermal sensitivity site of the EGIII variant. By modifying the site through substitution, binding of the component to the variant may be strengthened or diminished. For example, a non-aromatic residue in the binding crevice of EGIII may be substituted with phenylalanine or tyrosine to introduce aromatic side-chain stabilization where interaction of the cellulose substrate may interact favorably with the benzyl rings, increasing the stability of the EGIII variant.

(8) Increasing the electronegativity of any of the surfactant/ thermal sensitivity ligands may improve stability under surfactant or thermal stress. For example, substitution with phenylalanine or tyrosine may increase the electronegativity of D residues by improving shielding from solvent, thereby improving stability.

Variant EGIII

The present invention relates to the expression, purification and/or isolation and use of variant EGIII. These enzymes are preferably prepared by recombinant methods utilizing the gene identified and isolated according to the methods described below. However, enzymes for use in the present invention may be obtained by other art-recognized means such as purification from natural isolates.

Techniques that can be used to isolate EGIII encoding DNA sequences are well known in the art and include, but are not limited to, cDNA and/or genomic library screening with a homologous DNA probe and expression screening with activity assays or antibodies against EGIII. Any of these methods can be found in Sambrook, et al. or in *Current Protocols In Molecular Biology*, F. Ausubel, et al., ed. Greene Publishing and Wiley-Interscience, New York (1987) ("Ausubel").

After the isolation and cloning of the EGIII, other methods known in the art, such as site directed mutagenesis, are used to make the substitutions, additions or deletions that correspond to substituted amino acids in the expressed EGIII variant. Again, site directed mutagenesis and other methods of incorporating amino acid changes in expressed proteins at the DNA level can be found in Sambrook, et al. and Ausubel, et al.

After DNA sequences that encode the EGIII variants have been cloned into DNA constructs, the DNA is used to transform microorganisms. The microorganism to be transformed for the purpose of expressing a variant EGIII according to the present invention may advantageously comprise a strain derived from Trichoderma sp. Thus, a preferred mode for preparing variant EGIII cellulases according to the present invention comprises transforming a Trichoderma sp. host cell with a DNA construct comprising at least a fragment of DNA encoding a portion or of the variant EGIII. The DNA construct will generally be functionally attached to promoter. The transformed host cell is then grown under conditions so as to express he desired protein. Subsequently, the desired protein product is purified to substantial homogeneity.

However, it may in fact be that the best expression vehicle for a given DNA encoding a variant EGIII may differ from *T. reesei*. Thus, it may be that it will be most advantageous to express a protein in a transformation host that bears phylogenetic similarity to the source organism for the variant EGIII. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of a Trichoderma spp. expression system is provided for illustrative purposes only and as one option for expressing the variant EGIII of the invention. One of skill in the art, however, may be inclined to express the DNA encoding variant EGIII in a different host cell if appropriate and it should be understood that the source of the variant EGIII should be considered in determining the optimal expression host. Additionally, the skilled worker in the field will be capable of selecting the best expression system for a particular gene through routine techniques utilizing the tools available in the art.

In one embodiment, the strain comprises *T. reesei* (*reesei*), which is a useful strain for obtaining overexpressed protein. For example, RL-P37, described by Sheir-Neiss, et al.,*Appl. Microbiol. Biotechnol.* 20:46–53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant EGIII.

Where it is desired to obtain the variant EGIII in the absence of potentially detrimental native cellulolytic activity, it is useful to obtain a Trichoderma host cell strain which has had one or more cellulase genes deleted prior to introduction of a DNA construct or plasmid containing the DNA fragment encoding the variant EGIII. Such strains may be prepared by the method disclosed in U.S. Pat. No. 5,246,853 and WO 92/06209, which disclosures are hereby incorporated by reference. By expressing a variant EGIII cellulase in a host microorganism that is missing one or more cellulase genes, the identification and subsequent purification procedures are simplified. Any gene from Trichoderma sp. which has been cloned can be deleted, for example, the cbh1, cbh2, egl1, and egl3 genes as well as those encoding EGIII and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with Trichoderma sp., the selectable marker is chosen so that the presence of the selectable marker in the transformants will not significantly affect the properties thereof. Such a selectable marker may be a gene that encodes an assayable product. For example, a functional copy of a Trichoderma sp. gene may be used which if lacking in the host strain results in the host strain displaying an auxotrophic phenotype.

In a preferred embodiment, a pyr4⁻ derivative strain of Trichoderma sp. is transformed with a functional pyr4 gene, which thus provides a selectable marker for transformation. A pyr4⁻ derivative strain may be obtained by selection of Trichoderma sp. strains that are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, *Curr. Genet.* 19:359–365 (1991)). Selection of derivative strains is easily performed using the FOA resistance technique referred to above, and thus, the pyr4 gene is preferably employed as a selectable marker.

To transform pyr4⁻ Trichoderma sp. so as to be lacking in the ability to express one or more cellulase genes, a single DNA fragment comprising a disrupted or deleted cellulase gene is then isolated from the deletion plasmid and used to transform an appropriate pyr⁻ Trichoderma host. Transformants are then identified and selected based on their ability to express the pyr4 gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the pyr4 selectable markers.

Although the specific plasmid vectors described above relate to preparation of pyr⁻ transformants, the present invention is not limited to these vectors. Various genes can be deleted and replaced in the Trichoderma sp. strain using the above techniques. In addition, any available selectable markers can be used, as discussed above. In fact, any Trichoderma sp. gene that has been cloned, and thus identified, can be deleted from the genome using the above-described strategy.

As stated above, the host strains used are derivatives of Trichoderma sp. that lack or have a nonfunctional gene or genes corresponding to the selectable marker chosen. For example, if the selectable marker of pyr4 is chosen, then a specific pyr⁻ derivative strain is used as a recipient in the transformation procedure. Similarly, selectable markers comprising Trichoderma sp. genes equivalent to the *Aspergillus nidulans* genes amdS, argB, trpC, niaD may be used. The corresponding recipient strain must therefore be a derivative strain such as argB⁻, trpC⁻, niaD⁻, respectively.

DNA encoding the variant EGIII cellulase is then prepared for insertion into an appropriate microorganism. According to the present invention, DNA encoding a variant EGIII cellulase comprises the DNA necessary to encode for a protein that has functional cellulolytic activity. The DNA fragment or DNA variant fragment encoding the variant EGIII cellulase or derivative may be functionally attached to a fungal promoter sequence, for example, the promoter of the cbh1or egl1 gene.

It is also contemplated that more than one copy of DNA encoding a variant EGIII cellulase may be recombined into the strain to facilitate overexpression. The DNA encoding the variant EGIII cellulase may be prepared by the construction of an expression vector carrying the DNA encoding the cellulase. The expression vector carrying the inserted DNA fragment encoding the variant EGIII cellulase may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences. For example, pTEX is such a general-purpose expression vector. Genes or part thereof can be inserted downstream of the strong cbh1 promoter.

In the vector, the DNA sequence encoding the variant EGIII cellulase of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. The signal peptide provides for extracellular production of the variant EGIII cellulase or derivatives thereof. The DNA encoding the signal sequence is preferably that which is naturally associated with the gene to be expressed, however the signal sequence from any suitable source, for example an exo-cellobiohydrolase or endoglucanase from Trichoderma, is contemplated in the present invention.

The procedures used to ligate the DNA sequences coding for the variant EGIII cellulase of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in Trichoderma sp. is very low. Accordingly, uptake of the desired DNA sequence, gene or gene fragment is at best minimal. There are a number of methods to increase the permeability of the Trichoderma sp. cell wall in the derivative strain (i.e., lacking a functional gene corresponding to the used selectable marker) prior to the transformation process.

The preferred method in the present invention to prepare Trichoderma sp. for transformation involves the preparation of protoplasts from fungal mycelium. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host Trichoderma sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the Trichoderma sp. strain and the plasmid DNA is transferred to the nucleus. This fusion frequently leaves multiple copies of the plasmid DNA tenderly integrated into the host chromosome.

Usually a suspension containing the Trichoderma sp. protoplasts or cells that have been subjected to a permeability treatment at a density of $10^8$ to $10^9$/mL, preferably $2 \times 10^8$/mL are used in transformation. A volume of 100 $\mu$L of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if Pyr⁺ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the variant EGIII cellulases or derivatives thereof are recovered in active form from the host cell after growth in liquid media either as a result of the appropriate post translational processing of the novel variant EGIII cellulase or derivatives thereof.

The expressed variant EGIII cellulase may be recovered from the medium by conventional techniques including separations of the cells from the medium by centrifugation, filtration, and precipitation of the proteins in the supernatant or filtrate with a salt, for example, ammonium sulfate. Additionally, chromatography procedures such as ion exchange chromatography or affinity chromatography may be used. Antibodies (polyclonal or monoclonal) may be raised against the natural purified variant EGIII cellulase, or synthetic peptides may be prepared from portions of the variant EGIII cellulase molecule and used to raise polyclonal antibodies.

Compositions Comprising the EGIII
Variants of this Invention

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers. Immature cotton is significantly more amorphous than mature cotton and results in a lesser quality fabric when present due to, for example, uneven dyeing. The composition contemplated in the present invention further includes a cellulase component for use in washing of a soiled manufactured cellulose containing fabric. For example, the cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

Treating according to the instant invention comprises preparing an aqueous solution that contains an effective amount of cellulase together with other optional ingredients including, for example, a buffer, a surfactant, and/or a scouring agent. An effective amount of cellulase enzyme composition is a concentration of cellulase enzyme sufficient for its intended purpose. Thus, for example, an "effective amount" of cellulase in a stonewashing composition according to the present invention is that amount which will provide the desired effect, e.g., to produce a worn and faded look in the seams and on fabric panels. Similarly, an "effective amount" of cellulase in a composition intended for improving the feel and/or appearance of a cellulose containing fabric is that amount which will produce measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity which, in turn, depends on the nature of the cellulase employed. The exact concentration of buffer employed will depend on several factors that the skilled artisan can readily take into account. For example, in a preferred embodiment, the buffer, as well as the buffer concentration, is selected so as to maintain the pH of the final cellulase solution within the pH range required for optimal cellulase activity. The determination of the optimal pH range of the cellulases of the invention can be ascertained according to well-known techniques. Suitable buffers at pH within the activity range of the cellulase are well known to those skilled in the art in the field.

In addition to cellulase and a buffer, the treating composition may optionally contain a surfactant. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates will permit facile formulation of the cellulase solutions as well as permit feasible transportation of the composition to the location where it will be used. The treating concentrate can be in any art-recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283, which is incorporated herein by reference in its entirety.

Other materials can also be used with or placed in the cellulase composition of the present invention as desired, including stones, pumice, fillers, solvents, enzyme activators, and anti-redeposition agents depending on the eventual. use of the composition.

By way of example, stonewashing methods will be described in detail, however, the parameters described are readily modified by the skilled artisan for other applications, e.g., improving the feel and/or appearance of a fabric. The cellulose containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature that allow the cellulase enzyme to react efficiently with cellulose containing fabric, in this case to produce the stonewashed effect. However, such conditions are readily ascertainable by one of skill in the art. The reaction conditions effective for the stonewashing compositions of the present invention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., which conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all affect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal, antigraying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase-protecting agent. The granule can be formulated so as to contain materials to reduce the rate of dissolution of the granule into the wash medium. Such materials and granules are disclosed in U.S. Pat. No. 5,254,283, which is incorporated herein by reference in its entirety.

The detergent compositions of this invention employ a surface-active agent, e.g., surfactant, including anionic, nonionic and ampholytic surfactants well known for their, use in detergent compositions.

In order to further illustrate the present invention and advantages thereof, the following specific examples are given with the understanding that they are being offered to illustrate the present invention and should not be construed in any way as limiting its scope.

EXAMPLES

Example 1

Thermal Stability of EGIII Variants

Site-directed mutagenesis was performed to incorporate amino acid substitutions in *T. reesei* EGIII. The amino acids substituted into the EGIII were those at homologous locations in the Streptomyces 11AG8 homolog.

The following primers were used to produce substitutions in EGI from *T. reesei*. PCR was performed according to well-known techniques.

| Variant | Forward primer | Reverse Primer |
| --- | --- | --- |
| W7Y | GCT GTG ACC AGT ACG CAA CCT TCA C (SEQ ID NO: 1) | GTG AAG GTT GCG TAC TGG TCA CAG C (SEQ ID NO: 2) |
| G31Q | GCT CTG GAT TTC AGT GCG TGA CGG (SEQ ID NO: 3) | CCG TCA CGC ACT GAA ATC CAG AGC (SEQ ID NO: 4) |
| A35V | GCT GCG TGA CGG TGG TAT CGC TCA GC (SEQ ID NO: 5) | GCT GAG CGA TAC CAC CGT CAC GCA GC (SEQ ID NO: 6) |
| H45Q | GGG GCC AGT CTG CCT GCC AGG AGG CCC (SEQ ID NO: 7) | CCT CCT GGC AGG CAG ACT GGC (SEQ ID NO: 8) |
| S63V | CGT ACC AGA ACG TTC AGA TTG CCA TTC C (SEQ ID NO: 9) | GGA ATG GCA ATC TGA ACG TTC TGG TAC G (SEQ ID NO: 10) |
| S77G | CGT CAA CAG CAT CGG CAG CAT GCC C (SEQ ID NO: 11) | GGG CAT GCT GCC GAT GCT GTT GAC G (SEQ ID NO: 12) |
| M79I | GCA TCA GCA GCA TCC CCA CCA CTG (SEQ ID NO: 13) | CAG TGG TGG GGA TGC TGC TGA TGC (SEQ ID NO: 14) |
| H108R | CCA ACC CGA ATC GAG TCA CGT ACT CG (SEQ ID NO: 15) | CGA GTA CGT GAC TCG ATT CGG GTT GG (SEQ ID NO: 16) |
| T145E/ Y147W | CCA GAG CTG GGA GCT CTG GTA TGG CTA CAA CGG (SEQ ID NO: 17) | CCG TTG TAG CCA TAC CAG AGC TCC CAG CTC TGG (SEQ ID NO: 18) |
| M154N | GGC TAC AAC GGA GCC AAC CAA GTC TAT TCC TTT GTG G (SEQ ID NO: 19) | CCA CAA AGG AAT AGA CTT GGT TGG CTC CGT TGT AGC C (SEQ ID NO: 20) |
| Q162P | CCT TTG TGG CCC CGA CCA ACA CTA CC (SEQ ID NO: 21) | GGT AGT GTT GGT CGG GGC CAC AAA GG (SEQ ID NO: 22) |
| T163S | CCT TTG TGG CCC AGA GCA ACA CTA CC (SEQ ID NO: 23) | GGT AGT GTT GCT CTG GGC CAC AAA GG (SEQ ID NO: 24) |
| N167S | CCA ACA CTA CCA GCT ACA GCG GAG ATG (SEQ ID NO: 25) | CAT CTC CGC TGT AGC TGG TAG TGT TGG (SEQ ID NO: 26) |
| N174D | GGA GAT GTC AAG GAC TTC TTC AAT TAT CTC C (SEQ ID NO: 27) | GGA GAT AAT TGA AGA AGT CCT TGA CAT CTC C (SEQ ID NO: 28) |
| V192L | GGC CAA TAT CTT CTT AGC TAC G (SEQ ID NO: 29) | GGT AGC TAA GAA GAT ATT GGC C (SEQ ID NO: 30) |

Briefly, DNA that encodes *T. reesei* EG III was amplified from a cDNA clone (Ward, et al., *Proc. of the Tricel*

Symposium on "Trichoderma reesei cellulases and other hydrolases." Espoo, Finland 1993 Ed. Suominen, P. and Reinikanen, T. Foundation for Biotechnical and Industrial Research. 8, pp153–158; and U.S. Pat. No. 5,475,101) using PCR primers that introduced a Bgl II restriction endonuclease site at the 5' end of the egl3 gene (immediately upstream of the first ATG codon) and an Xba I site at the 3' end (immediately downstream of the "stop" codon). The amplified fragment was then digested with Bgl II and Xba I, and ligated into pUC 19 digested with Bgl II and Xba I.

Variants were made in this plasmid using the QuikChange™ mutagenesis methods (Stratagene). The variant genes were then subcloned into the Aspergillus expression vector pGAPT-pyrG. This is a variant of PGPT-pyrG (Berka and Barnett, *Biotech.Adv.* 7:127 (1989)) in which non-essential DNA has been excised. Vectors carrying the variant genes were then transformed into *A. niger* var. awamori and the resultant strains grown in shake-flask cultures (WO 98/31821).

EG III variants were then purified from cell-free supernatants of these cultures by column chromatography. Briefly, approximately 1 mL of Pharmacia Butyl Sepharose (Fast Flow) resin per 10 mg of EGIII was loaded into a disposable drip column with 0.5 M. ammonium sulfate. The column was then equilibrated with 0.05 M Bis Tris Propane and 0.05 M anmmoniaum acetate at pH 8.

The EGIII-like cellulase containing supernatants were treated overnight with 0.18 mg/mL of endoglucanase H at 37° C. Ammonium sulfate was added to the treated supernatants to a final concentration of approximately 0.5 M. After centrifugation, the supernatant was loaded onto the column. The column was then washed with 3 volumes equilibration buffer and then eluted with 2×1 volumes of 0.05 M Bis Tris Propane and 0.05 M ammonium acetate, pH 8. Each volume of flow through was collected as a separate fraction with the EGIII-like cellulase appearing in the second fraction.

Equilibrium CD experiments were performed on an Aviv 62DS or 62ADS spectrophotometer, equipped with a 5 position thermoelectric cell holder supplied by Aviv. Buffer conditions were 50 mM bis-tris propane and 50 mM ammonium acetate adjusted to pH 8.0 with acetic acid. The final protein concentration for each experiment was in the range of 5–30 mM. Data was collected in a 0.1 cm path length cell.

Spectra were collected from 265–210 nm. Thermal denaturations were performed at 217 nm from 30 to 90° C. with data collected every two degrees. The equilibration time at each temperature was 0.1 minutes and data was collected for 4 seconds per sample.

The melting points were determined according to the methods of Luo, et al., *Biochemistry* 34:10669 and Gloss, et al., *Biochemistry* 36:5612.

TABLE 2

Thermal stability of EGIII variants

| Amino acid substitutions | Δ $T_m$ | Tm (° C.) | Fit error |
|---|---|---|---|
| *T. reesei* EGIII | 0.00 | 54.43 | 0.2 |
| W7Y | −1.03 | 53.40 | 0.24 |
| G31Q | −14.03 | 40.40 | 0.15 |
| A35V | 7.40 | 61.83 | 0.23 |
| H45Q | 0.47 | 54.90 | 0.06 |
| S63V | −0.83 | 53.60 | 0.11 |
| S77G | 0.07 | 54.50 | 0.09 |
| M79I | −7.13 | 47.30 | 0.27 |
| H108R | 0.87 | 55.30 | 0.37 |
| T145E/Y147W | 0.77 | 55.20 | 0.05 |
| M154N | 1.37 | 55.80 | 0.15 |
| Q162P | 0.07 | 54.50 | 0.19 |
| T163S | 0.27 | 54.70 | 0.07 |
| N167S | 0.17 | 54.60 | 0.10 |
| N174D | 1.17 | 55.60 | 0.44 |
| V192L | −0.23 | 54.20 | 0.13 |

From Table 2 it can be seen that some mutations caused a significant increase in thermal stability. For example, changing the alanine at position 35 to a valine increased the melting point by 7.4° C.

Example 3

Specific Activity of EGIII-like Cellulases

To assay for specific activity, a NPC hydrolysis assay was used. In a microtiter plate, 100 μl 50 mM sodium acetate, pH 5.5 and 20 μl 25 mg/mL o-NPC (o-Nitrophenyl o-D-Cellobioside (Sigma N 4764)) in assay buffer was added. The plate was incubated for 10 minutes at 40° C.

Once equilibrated, 10 μL EGIII-like cellulase was added and the plate incubated at 40° C. for another 10 minutes. To quench the hydrolysis and stop the reaction, 70 μL of 0.2 M glycine, pH 10.0 was added. The plate was then read in a microtiter plate reader at 410 nm. As a guide, 10 μl of a 0.1 mg/ml solution of *T. reesei* EGIII provided an OD of around 0.3.

The concentration of EGIII-like cellulase was determined by absorbance at 280 nm where the extinction coefficient was 78711 $M^{-1}$ $cm^{-1}$ or 3.352 $g/L^{-1}$ experimentally determined by the method of Edelhoch as described in Pace, et al., *Pro. Sci.* 4:2411 (1995).

TABLE 3

Specific Activity of EGIII-like Cellulases

| EGIII-like Cellulase | Tm (° C.) | Specific Activity (relative to WT) |
|---|---|---|
| WT | 54.4 | 1.00 |
| W7Y | 53.4 | 1.03 |
| G31Q | 40.4 | 0.19 |
| A35V | 61.8 | 0.83 |
| H45Q | 54.9 | 1.08 |
| S63V | 53.6 | 0.69 |
| S77G | 54.5 | 1.02 |
| M79I | 47.3 | 0.44 |
| H108R | 55.3 | 0.85 |
| T145E/Y147W | | 0.80 |
| | | 0.83 |
| M154N | 55.8 | 0.14 |
| Q162P | 54.5 | 0.99 |
| T163S | 54.7 | 1.00 |
| N167S | 54.6 | 0.95 |
| N174D | 55.6 | 0.86 |
| V192L | 54.2 | 1.13 |

As can be seen from Table 3, the mutations that stabilized the variant EGIII cellulases derived from EGIII tend to retain activity. The change at position 31 to glutamine, which significantly decreased thermal stability also significantly decreased activity.

SEQUENCE LISTING

<160> NUMBER OF SEQ ID NOS: 54

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
gctgtgacca gtacgcaacc ttcac                               25

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
gtgaaggttg cgtactggtc acagc                               25

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
gctctggatt tcagtgcgtg acgg                                24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
ccgtcacgca ctgaaatcca gagc                                24

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
gctgcgtgac ggtggtatcg ctcagc                              26

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6
gctgagcgat accaccgtca cgcagc                              26

<210> SEQ ID NO 7
<211> LENGTH: 27

```
<212> TYPE: DNA
<213> ORGANISM: Artificial Sequence
<220> FEATURE:
<223> OTHER INFORMATION: primer

<400> SEQUENCE: 7 gggccagtc tgcctgccag gaggccc                                27

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
cctcctggca ggcagactgg c                                     21

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
cgtaccagaa cgttcagatt gccattcc                              28

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
ggaatggcaa tctgaacgtt ctggtacg                              28

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
cgtcaacagc atcggcagca tgccc                                 25

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
gggcatgctg ccgatgctgt tgacg                                 25

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
```

```
gcatcagcag catccccacc actg                                              24
```

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14

```
cagtggtggg gatgctgctg atgc                                              24
```

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15

```
ccaacccgaa tcgagtcacg tactcg                                            26
```

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16

```
cgagtacgtg actcgattcg ggttgg                                            26
```

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17

```
ccagagctgg gagctctggt atggctacaa cgg                                    33
```

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18

```
ccgttgtagc cataccagag ctcccagctc tgg                                    33
```

<210> SEQ ID NO 19
<211> LENGTH: 37
<212> TYPE: DNA
<213> ORGANISM: Artificial Sequence
<220> FEATURE:
<223> OTHER INFORMATION: primer

<400> SEQUENCE: 19

```
ggctacaacg gagccaacca agtctattcc tttgtgg                                37
```

<210> SEQ ID NO 20
<211> LENGTH: 37
<212> TYPE: DNA
<213> ORGANISM: Artificial Sequence

```
<220> FEATURE:
<223> OTHER INFORMATION: primer

<400> SEQUENCE: 20
ccacaaagga atagacttgg ttggctccgt tgtagcc                              37

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
cctttgtggc cccgaccaac actacc                                         26

<210> SEQ ID NO 22
<211> LENGTH: 26
<212> TYPE: DNA
<213> ORGANISM: Artificial Sequence
<220> FEATURE:
<223> OTHER INFORMATION: primer

<400> SEQUENCE: 22
ggtagtgttg gtcggggcca caaagg                                         26

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
cctttgtggc ccagagcaac actacc                                         26

<210> SEQ ID NO 24
<211> LENGTH: 26
<212> TYPE: DNA
<213> ORGANISM: Artificial Sequence
<220> FEATURE:
<223> OTHER INFORMATION: primer

<400> SEQUENCE: 24
ggtagtgttg ctctgggcca caaagg                                         26

<210> SEQ ID NO 25
<211> LENGTH: 27
<212> TYPE: DNA
<213> ORGANISM: Artificial Sequence
<220> FEATURE:
<223> OTHER INFORMATION: primer

<400> SEQUENCE: 25
ccaacactac cagctacagc ggagatg                                        27

<210> SEQ ID NO 26
<211> LENGTH: 27
<212> TYPE: DNA
<213> ORGANISM: Artificial Sequence
<220> FEATURE:
<223> OTHER INFORMATION: primer

<400> SEQUENCE: 26
catctccgct gtagctggta gtgttgg                                        27
```

<210> SEQ ID NO 27
<211> LENGTH: 31
<212> TYPE: DNA
<213> ORGANISM: Artificial Sequence
<220> FEATURE:
<223> OTHER INFORMATION: primer

<400> SEQUENCE: 27
ggagatgtca aggacttctt caattatctc c           31

<210> SEQ ID NO 28
<211> LENGTH: 31
<212> TYPE: DNA
<213> ORGANISM: Artificial Sequence
<220> FEATURE:
<223> OTHER INFORMATION: primer

<400> SEQUENCE: 28
ggagataatt gaagaagtcc ttgacatctc c           31

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
ggccaatatc ttcttagcta cg                     22

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
ggtagctaag aagatattgg cc                     22

<210> SEQ ID NO 31
<211> LENGTH: 218
<212> TYPE: PRT
<213> ORGANISM: Trichoderma reesei

<400> SEQUENCE: 31

Gln Thr Ser Cys Asp Gln Trp Ala Thr Phe Thr Gly Asn Gly Tyr Thr
 1               5                  10                  15

Val Ser Asn Asn Leu Trp Gly Ala Ser Ala Gly Ser Gly Phe Gly Cys
            20                  25                  30

Val Thr Ala Val Ser Leu Ser Gly Gly Ala Ser Trp His Ala Asp Trp
        35                  40                  45

Gln Trp Ser Gly Gly Gln Asn Asn Val Lys Ser Tyr Gln Asn Ser Gln
    50                  55                  60

Ile Ala Ile Pro Gln Lys Arg Thr Val Asn Ser Ile Ser Ser Met Pro
65                  70                  75                  80

Thr Thr Ala Ser Trp Ser Tyr Ser Gly Ser Asn Ile Arg Ala Asn Val
                85                  90                  95

Ala Tyr Asp Leu Phe Thr Ala Ala Asn Pro Asn His Val Thr Tyr Ser
            100                 105                 110

Gly Asp Tyr Glu Leu Met Ile Trp Leu Gly Lys Tyr Gly Asp Ile Gly
        115                 120                 125

-continued

```
Pro Ile Gly Ser Ser Gln Gly Thr Val Asn Val Gly Gly Gln Ser Trp
    130                 135                 140

Thr Leu Tyr Tyr Gly Tyr Asn Gly Ala Met Gln Val Tyr Ser Phe Val
145                 150                 155                 160

Ala Gln Thr Asn Thr Thr Asn Tyr Ser Gly Asp Val Lys Asn Phe Phe
                165                 170                 175

Asn Tyr Leu Arg Asp Asn Lys Gly Tyr Asn Ala Ala Gly Gln Tyr Val
            180                 185                 190

Leu Ser Tyr Gln Phe Gly Thr Glu Pro Phe Thr Gly Ser Gly Thr Leu
        195                 200                 205

Asn Val Ala Ser Trp Thr Ala Ser Ile Asn
    210                 215

<210> SEQ ID NO 32
<211> LENGTH: 702
<212> TYPE: DNA
<213> ORGANISM: Trichoderma reesei

<400> SEQUENCE: 32
atgaagttcc ttcaagtcct ccctgccctc ataccggccg ccctggccca aaccagctgt     60
gaccagtggg caaccttcac tggcaacggc tacacagtca gcaacaacct tggggagca    120 tcagccggct ctggatttgg ctgcgtgacg gcggtatcgc tcagcggcgg ggcctcctgg    180
cacgcagact ggcagtggtc cggcggccag aacaacgtca agtcgtacca gaactctcag    240
attgccattc cccagaagag gaccgtcaac agcatcagca gcatgcccac cactgccagc    300
tggagctaca gcgggagcaa catccgcgct aatgttgcgt atgacttgtt cacccgcagcc    360 aacccgaatc atgtcacgta ctcgggagac tacgaactca tgatctggct tggcaaatac    420
ggcgatattg gccgattggg gtcctcacag ggaacagtca acgtcggtgg ccagagctgg    480
acgctctact atggctacaa cggagccatg caagtctatt cctttgtggc ccagaccaac    540
actaccaact acagcggaga tgtcaagaac ttcttcaatt atctccgaga caataaagga    600
tacaacgctg caggccaata tgttcttagc taccaatttg gtaccgagcc cttcacgggc    660
agtggaactc tgaacgtcgc atcctggacc gcatctatca ac                       702

<210> SEQ ID NO 33
<211> LENGTH: 234
<212> TYPE: PRT
<213> ORGANISM: Trichoderma reesei

<400> SEQUENCE: 33

Met Lys Phe Leu Gln Val Leu Pro Ala Leu Ile Pro Ala Ala Leu Ala
  1               5                  10                  15

Gln Thr Ser Cys Asp Gln Trp Ala Thr Phe Thr Gly Asn Gly Tyr Thr
             20                  25                  30

Val Ser Asn Asn Leu Trp Gly Ala Ser Ala Gly Ser Gly Phe Gly Cys
         35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110
```

```
Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
        180                 185                 190

Asn Tyr Leu Arg Asp Asn Lys Gly Tyr Asn Ala Ala Gly Gln Tyr Val
                195                 200                 205

Leu Ser Tyr Gln Phe Gly Thr Glu Pro Phe Thr Gly Ser Gly Thr Leu
        210                 215                 220

Asn Val Ala Ser Trp Thr Ala Ser Ile Asn
225                 230
```

<210> SEQ ID NO 34
<211> LENGTH: 234
<212> TYPE: PRT
<213> ORGANISM: Hypocrea schweinitzii

<400> SEQUENCE: 34

```
Met Lys Phe Leu Gln Val Leu Pro Ala Ile Leu Pro Ala Ala Leu Ala
1               5                   10                  15

Gln Thr Ser Cys Asp Gln Tyr Ala Thr Phe Ser Gly Asn Gly Tyr Ile
            20                  25                  30

Val Ser Asn Asn Leu Trp Gly Ala Ser Ala Gly Ser Gly Phe Gly Cys
        35                  40                  45

Val Thr Ser Val Ser Leu Asn Gly Ala Ala Ser Trp His Ala Asp Trp
    50                  55                  60

Gln Trp Ser Gly Gly Gln Asn Asn Val Lys Ser Tyr Gln Asn Val Gln
65                  70                  75                  80

Ile Asn Ile Pro Gln Lys Arg Thr Val Asn Ser Ile Gly Ser Met Pro
                85                  90                  95

Thr Thr Ala Ser Trp Ser Tyr Ser Gly Ser Asp Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
130                 135                 140

Pro Ile Gly Ser Ser Gln Gly Thr Val Asn Val Gly Gly Gln Thr Trp
145                 150                 155                 160

Thr Leu Tyr Tyr Gly Tyr Asn Gly Ala Met Gln Val Tyr Ser Phe Val
                165                 170                 175

Ala Gln Ser Asn Thr Thr Ser Tyr Ser Gly Asp Val Lys Asn Phe Phe
        180                 185                 190

Asn Tyr Leu Arg Asp Asn Lys Gly Tyr Asn Ala Gly Gly Gln Tyr Val
                195                 200                 205

Leu Ser Tyr Gln Phe Gly Thr Glu Pro Phe Thr Gly Ser Gly Thr Leu
        210                 215                 220

Asn Val Ala Ser Trp Thr Ala Ser Ile Asn
225                 230
```

-continued

```
<210> SEQ ID NO 35
<211> LENGTH: 259
<212> TYPE: PRT
<213> ORGANISM: Aspergillus aculeatus

<400> SEQUENCE: 35

Met Lys Ala Phe His Leu Leu Ala Ala Leu Ala Gly Ala Ala Val Ala
 1               5                  10                  15

Gln Gln Ala Gln Leu Cys Asp Gln Tyr Ala Thr Tyr Thr Gly Gly Val
             20                  25                  30

Tyr Thr Ile Asn Asn Leu Trp Gly Lys Asp Ala Gly Ser Gly Ser
         35                  40                  45

Gln Cys Thr Thr Val Asn Ser Ala Ser Ser Ala Gly Thr Ser Trp Ser
     50                  55                  60

Thr Lys Trp Asn Trp Ser Gly Gly Glu Asn Ser Val Lys Ser Tyr Ala
 65                  70                  75                  80

Asn Ser Gly Leu Thr Phe Asn Lys Lys Leu Val Ser Gln Ile Ser Gln
                 85                  90                  95

Ile Pro Thr Thr Ala Arg Trp Ser Tyr Asp Asn Thr Gly Ile Arg Ala
            100                 105                 110

Asp Val Ala Tyr Asp Leu Phe Thr Ala Ala Asp Ile Asn His Val Thr
        115                 120                 125

Trp Ser Gly Asp Tyr Glu Leu Met Ile Trp Leu Ala Arg Tyr Gly Gly
    130                 135                 140

Val Gln Pro Ile Gly Ser Gln Ile Ala Thr Ala Thr Val Asp Gly Gln
145                 150                 155                 160

Thr Trp Glu Leu Trp Tyr Gly Ala Asn Gly Ser Gln Lys Thr Tyr Ser
                165                 170                 175

Phe Val Ala Pro Thr Pro Ile Thr Ser Phe Gln Gly Asp Val Asn Asp
            180                 185                 190

Phe Phe Lys Tyr Leu Thr Gln Asn His Gly Phe Pro Ala Ser Ser Gln
        195                 200                 205

Tyr Leu Ile Thr Leu Gln Phe Gly Thr Glu Pro Phe Thr Gly Gly Pro
    210                 215                 220

Ala Thr Leu Ser Val Ser Asn Trp Ser Ala Ser Val Gln Gln Ala Gly
225                 230                 235                 240

Phe Glu Pro Trp Gln Asn Gly Ala Gly Leu Ala Val Asn Ser Phe Ser
                245                 250                 255

Ser Thr Val

<210> SEQ ID NO 36
<211> LENGTH: 239
<212> TYPE: PRT
<213> ORGANISM: Aspergillus kawachii (1)

<400> SEQUENCE: 36

Met Lys Leu Ser Met Thr Leu Ser Leu Phe Ala Ala Thr Ala Met Gly
 1               5                  10                  15

Gln Thr Met Cys Ser Gln Tyr Asp Ser Ala Ser Ser Pro Pro Tyr Ser
             20                  25                  30

Val Asn Gln Asn Leu Trp Gly Glu Tyr Gln Gly Thr Gly Ser Gln Cys
         35                  40                  45

Val Tyr Val Asp Lys Leu Ser Ser Ser Gly Ala Ser Trp His Thr Lys
     50                  55                  60

Trp Thr Trp Ser Gly Gly Glu Gly Thr Val Lys Ser Tyr Ser Asn Ser
 65                  70                  75                  80
```

-continued

```
Gly Leu Thr Phe Asp Lys Lys Leu Val Ser Asp Val Ser Ser Ile Pro
                85                  90                  95

Thr Ser Val Thr Trp Ser Gln Asp Thr Asn Val Gln Ala Asp Val
            100                 105                 110

Ser Tyr Asp Leu Phe Thr Ala Ala Asn Ala Asp His Ala Thr Ser Ser
            115                 120                 125

Gly Asp Tyr Glu Leu Met Ile Trp Leu Ala Arg Tyr Gly Ser Val Gln
    130                 135                 140

Pro Ile Gly Lys Gln Ile Ala Thr Ala Thr Val Gly Gly Lys Ser Trp
145                 150                 155                 160

Glu Val Trp Tyr Gly Thr Ser Thr Gln Ala Gly Ala Glu Gln Lys Thr
                165                 170                 175

Tyr Ser Phe Val Ala Gly Ser Pro Ile Asn Ser Trp Ser Gly Asp Ile
            180                 185                 190

Lys Asp Phe Phe Asn Tyr Leu Thr Gln Asn Gln Gly Phe Pro Ala Ser
            195                 200                 205

Ser Gln His Leu Ile Thr Leu Gln Cys Gly Thr Glu Pro Phe Thr Gly
    210                 215                 220

Gly Pro Ala Thr Phe Thr Val Asp Asn Trp Thr Ala Ser Val Asn
225                 230                 235
```

<210> SEQ ID NO 37
<211> LENGTH: 239
<212> TYPE: PRT
<213> ORGANISM: Aspergillus kawachii (2)

<400> SEQUENCE: 37

```
Met Lys Ala Phe His Leu Leu Ala Ala Leu Ser Gly Ala Ala Val Ala
1               5                   10                  15

Gln Gln Ala Gln Leu Cys Asp Gln Tyr Ala Thr Tyr Thr Gly Gly Val
            20                  25                  30

Tyr Thr Ile Asn Asn Asn Leu Trp Gly Lys Asp Ala Gly Ser Gly Ser
        35                  40                  45

Gln Cys Thr Thr Val Asn Ser Ala Ser Ser Ala Gly Thr Ser Trp Ser
50                  55                  60

Thr Lys Trp Asn Trp Ser Gly Gly Glu Asn Ser Val Lys Ser Tyr Ala
65                  70                  75                  80

Asn Ser Gly Leu Ser Phe Asn Lys Lys Leu Val Ser Gln Ile Ser His
            85                  90                  95

Ile Pro Thr Ala Ala Arg Trp Ser Tyr Asp Asn Thr Cys Ile Arg Arg
            100                 105                 110

Gly Arg Ala Tyr Asp Leu Phe Thr Ala Ala Asp Ile Asn His Val Thr
        115                 120                 125

Trp Ser Gly Asp Tyr Glu Leu Met Ile Trp Leu Ala Arg Tyr Gly Gly
    130                 135                 140

Val Gln Pro Leu Gly Ser Gln Ile Ala Thr Ala Thr Val Glu Gly Gln
145                 150                 155                 160

Thr Trp Glu Leu Trp Tyr Gly Val Asn Gly Ala Gln Lys Thr Tyr Ser
                165                 170                 175

Phe Val Ala Ala Asn Pro Ile Thr Ser Phe Gln Gly Asp Ile Asn Asp
            180                 185                 190

Phe Phe Lys Tyr Leu Thr Gln Asn His Gly Phe Pro Ala Ser Ser Gln
            195                 200                 205

Tyr Leu Ile Ile Leu Ala Leu Gln Phe Gly Thr Glu Pro Phe Thr Gly
```

```
                 210                 215                 220

Gly Pro Ala Thr Leu Asn Val Ala Asp Trp Ser Ala Ser Val Gln
225                 230                 235

<210> SEQ ID NO 38
<211> LENGTH: 247
<212> TYPE: PRT
<213> ORGANISM: Aspergillus oryzae

<400> SEQUENCE: 38

Met Lys Leu Ser Leu Ala Leu Ala Thr Leu Val Ala Thr Ala Phe Ser
  1               5                  10                  15

Gln Glu Leu Cys Ala Gln Tyr Asp Ser Ala Ser Ser Pro Pro Tyr Ser
                 20                  25                  30

Val Asn Asn Asn Leu Trp Gly Gln Asp Ser Gly Thr Gly Phe Thr Ser
             35                  40                  45

Gln Cys Val Tyr Val Asp Asn Leu Ser Ser Ser Gly Ala Ala Trp His
 50                  55                  60

Thr Thr Trp Thr Trp Asn Gly Gly Glu Gly Ser Val Lys Ser Tyr Ser
 65                  70                  75                  80

Asn Ser Ala Val Thr Phe Asp Lys Lys Leu Val Ser Asp Val Gln Ser
                 85                  90                  95

Ile Pro Thr Asp Val Glu Trp Ser Gln Asp Phe Thr Asn Thr Asn Val
                100                 105                 110

Asn Ala Asp Val Ala Tyr Asp Leu Phe Thr Ala Ala Asp Gln Asn His
            115                 120                 125

Val Thr Tyr Ser Gly Asp Tyr Glu Leu Met Ile Trp Leu Ala Arg Tyr
130                 135                 140

Gly Thr Ile Gln Pro Ile Gly Thr Gln Ile Asp Thr Ala Thr Val Glu
145                 150                 155                 160

Gly His Thr Trp Glu Leu Trp Phe Thr Tyr Gly Thr Thr Ile Gln Ala
                165                 170                 175

Gly Ala Glu Gln Lys Thr Tyr Ser Phe Val Ser Ala Thr Pro Ile Asn
            180                 185                 190

Thr Phe Gly Gly Asp Ile Lys Lys Phe Phe Asp Tyr Ile Thr Ser Lys
        195                 200                 205

His Ser Phe Pro Ala Ser Ala Gln Tyr Leu Ile Asn Met Gln Phe Gly
210                 215                 220

Thr Glu Pro Phe Phe Thr Thr Gly Gly Pro Val Thr Phe Thr Val Pro
225                 230                 235                 240

Asn Trp Thr Ala Ser Val Asn
                245

<210> SEQ ID NO 39
<211> LENGTH: 254
<212> TYPE: PRT
<213> ORGANISM: Humicola grisea

<400> SEQUENCE: 39

Met Leu Lys Ser Ala Leu Leu Leu Gly Ala Ala Ala Val Ser Val Gln
  1               5                  10                  15

Ser Ala Ser Ile Pro Thr Ile Pro Ala Asn Leu Glu Pro Arg Gln Ile
                 20                  25                  30

Arg Ser Leu Cys Glu Leu Tyr Gly Tyr Trp Ser Gly Asn Gly Tyr Glu
             35                  40                  45

Leu Leu Asn Asn Leu Trp Gly Lys Asp Thr Ala Thr Ser Gly Trp Gln
```

```
                50                  55                  60
Cys Thr Tyr Leu Asp Gly Thr Asn Asn Gly Gly Ile Gln Trp Ser Thr
 65                  70                  75                  80

Ala Trp Glu Trp Gln Gly Ala Pro Asp Asn Val Lys Ser Tyr Pro Tyr
                 85                  90                  95

Val Gly Lys Gln Ile Gln Arg Gly Arg Lys Ile Ser Asp Ile Asn Ser
                100                 105                 110

Met Arg Thr Ser Val Ser Trp Thr Tyr Asp Arg Thr Asp Ile Arg Ala
                115                 120                 125

Asn Val Ala Tyr Asp Val Phe Thr Ala Arg Asp Pro Asp His Pro Asn
                130                 135                 140

Trp Gly Gly Asp Tyr Glu Leu Met Ile Trp Leu Ala Arg Tyr Gly Gly
145                 150                 155                 160

Ile Tyr Pro Ile Gly Thr Phe His Ser Gln Val Asn Leu Ala Gly Arg
                165                 170                 175

Thr Trp Asp Leu Trp Thr Gly Tyr Asn Gly Asn Met Arg Val Tyr Ser
                180                 185                 190

Phe Leu Pro Pro Ser Gly Asp Ile Arg Asp Phe Ser Cys Asp Ile Lys
                195                 200                 205

Asp Phe Phe Asn Tyr Leu Glu Arg Asn His Gly Tyr Pro Ala Arg Glu
210                 215                 220

Gln Asn Leu Ile Val Tyr Gln Val Gly Thr Glu Cys Phe Thr Gly Gly
225                 230                 235                 240

Pro Ala Arg Phe Thr Cys Arg Asp Phe Arg Ala Asp Leu Trp
                245                 250

<210> SEQ ID NO 40
<211> LENGTH: 254
<212> TYPE: PRT
<213> ORGANISM: Humicola insolens

<400> SEQUENCE: 40

Met Leu Lys Ser Ala Leu Leu Gly Pro Ala Ala Val Ser Val Gln
 1               5                  10                  15

Ser Ala Ser Ile Pro Thr Ile Pro Ala Asn Leu Glu Pro Arg Gln Ile
                 20                  25                  30

Arg Ser Leu Cys Glu Leu Tyr Gly Tyr Trp Ser Gly Asn Gly Tyr Glu
                 35                  40                  45

Leu Leu Asn Asn Leu Trp Gly Lys Asp Thr Ala Thr Ser Gly Trp Gln
 50                  55                  60

Cys Thr Tyr Leu Asp Gly Thr Asn Asn Gly Gly Ile Gln Trp Ser Thr
 65                  70                  75                  80

Ala Trp Glu Trp Gln Gly Ala Pro Asp Asn Val Lys Ser Tyr Pro Tyr
                 85                  90                  95

Val Gly Lys Gln Ile Gln Arg Gly Arg Lys Ile Ser Asp Ile Asn Ser
                100                 105                 110

Met Arg Thr Ser Val Ser Trp Thr Tyr Asp Arg Thr Asp Ile Arg Ala
                115                 120                 125

Asn Val Ala Tyr Asp Val Phe Thr Ala Arg Asp Pro Asp His Pro Asn
                130                 135                 140

Trp Gly Gly Asp Tyr Glu Leu Met Ile Trp Leu Ala Arg Tyr Gly Gly
145                 150                 155                 160

Ile Tyr Pro Ile Gly Thr Phe His Ser Gln Val Asn Leu Ala Gly Arg
                165                 170                 175
```

```
Thr Trp Asp Leu Trp Thr Gly Tyr Asn Gly Asn Met Arg Val Tyr Ser
            180                 185                 190

Phe Leu Pro Pro Ser Gly Asp Ile Arg Asp Phe Ser Cys Asp Ile Lys
            195                 200                 205

Asp Phe Phe Asn Tyr Leu Glu Arg Asn His Gly Tyr Pro Ala Arg Glu
210                 215                 220

Gln Asn Leu Ile Val Tyr Gln Val Gly Thr Glu Cys Phe Thr Gly Gly
225                 230                 235                 240

Pro Ala Arg Phe Thr Cys Arg Asp Phe Arg Ala Asp Leu Trp
            245                 250

<210> SEQ ID NO 41
<211> LENGTH: 247
<212> TYPE: PRT
<213> ORGANISM: Chaetomium brasilliense

<400> SEQUENCE: 41

Met Lys Leu Thr Leu Val Leu Phe Val Ser Ser Leu Ala Ala Ala Thr
1               5                   10                  15

Pro Leu Gly Trp Arg Glu Arg Gln Gln Val Ser Leu Cys Gly Gln
            20                  25                  30

Ser Ser Ser Trp Ser Gly Asn Gly Tyr Gln Leu Asn Asn Asn Leu Trp
            35                  40                  45

Gly Gln Ser Arg Ala Thr Ser Gly Ser Gln Cys Thr Tyr Leu Asp Ser
50                  55                  60

Ser Ser Asn Ser Gly Ile His Trp His Thr Thr Trp Thr Trp Glu Gly
65                  70                  75                  80

Gly Glu Gly Glu Val Lys Ser Tyr Ala Tyr Ser Gly Arg Gln Val Ser
                85                  90                  95

Thr Gly Leu Thr Ile Ala Ser Ile Asp Ser Met Gln Thr Ser Val Ser
            100                 105                 110

Trp Glu Tyr Asn Thr Thr Asp Ile Gln Ala Asn Val Ala Tyr Asp Ile
            115                 120                 125

Phe Thr Ala Glu Asp Pro Asp His Glu His Ser Ser Gly Asp Tyr Glu
            130                 135                 140

Leu Met Ile Trp Leu Ala Arg Tyr Asn Asn Val Ser Pro Ile Gly Ser
145                 150                 155                 160

Ser Val Ala Thr Ala Thr Val Gly Gly Asp Thr Trp Asp Leu Phe Ala
                165                 170                 175

Gly Ala Asn Gly Asp Met Glu Val Tyr Ser Phe Val Ala Glu Asn Thr
            180                 185                 190

Met Asn Ser Phe Ser Gly Asp Val Lys Asp Phe Asp Tyr Leu Glu
            195                 200                 205

Gln Asn Val Gly Phe Pro Val Asp Asp Gln Tyr Leu Leu Val Phe Glu
210                 215                 220

Leu Gly Ser Glu Ala Phe Thr Gly Gly Pro Ala Thr Leu Ser Val Ser
225                 230                 235                 240

Gln Phe Ser Ala Asn Ile Ala
            245

<210> SEQ ID NO 42
<211> LENGTH: 238
<212> TYPE: PRT
<213> ORGANISM: Fusarium equiseti

<400> SEQUENCE: 42
```

```
Met Lys Ser Thr Leu Leu Ala Gly Ala Phe Ala Pro Leu Ala Phe
 1               5                  10                  15

Ala Lys Asp Leu Cys Glu Gln Tyr Gly Tyr Leu Ser Ser Asp Gly Tyr
             20                  25                  30

Ser Leu Asn Asn Val Trp Gly Lys Asp Ser Gly Thr Gly Asp Gln
         35                  40                  45

Cys Thr His Val Asn Trp Asn Asn Ala Asn Gly Ala Gly Trp Asp Val
     50                  55                  60

Glu Trp Asn Trp Ser Gly Gly Lys Asp Asn Val Lys Ser Tyr Pro Asn
 65                  70                  75                  80

Ser Ala Leu Leu Ile Gly Glu Asp Lys Lys Thr Ile Ser Ser Ile Thr
                 85                  90                  95

Asn Met Gln Ser Thr Ala Glu Trp Lys Tyr Ser Gly Asp Asn Leu Arg
             100                 105                 110

Ala Asp Val Ala Tyr Asp Leu Phe Thr Ala Ala Asp Pro Asn His Glu
         115                 120                 125

Thr Ser Ser Gly Glu Tyr Glu Leu Met Val Trp Leu Ala Arg Ile Gly
130                 135                 140

Gly Val Gln Pro Ile Gly Ser Leu Gln Thr Ser Val Thr Ile Glu Gly
145                 150                 155                 160

His Thr Trp Glu Leu Trp Val Gly Met Asn Gly Ser Met Lys Val Phe
                 165                 170                 175

Ser Phe Val Ala Pro Thr Pro Val Asn Asn Phe Asn Ala Asp Ile Lys
             180                 185                 190

Gln Phe Trp Asp Tyr Leu Thr Lys Ser Gln Asn Phe Pro Ala Asp Asn
         195                 200                 205

Gln Tyr Leu Leu Thr Phe Gln Phe Gly Thr Glu Pro Phe Thr Gly Asp
     210                 215                 220

Asn Ala Lys Phe Thr Val Thr Asn Phe Asn Ala His Leu Lys
225                 230                 235

<210> SEQ ID NO 43
<211> LENGTH: 244
<212> TYPE: PRT
<213> ORGANISM: Fusarium javanicum (1)

<400> SEQUENCE: 43

Met Lys Ser Ala Ile Val Ala Ala Leu Ala Gly Leu Ala Ala Ser
 1               5                  10                  15

Pro Thr Arg Leu Ile Pro Arg Gly Gln Phe Cys Gly Gln Trp Asp Ser
             20                  25                  30

Glu Thr Ala Gly Ala Tyr Thr Ile Tyr Asn Asn Leu Trp Gly Lys Asp
         35                  40                  45

Asn Ala Glu Ser Gly Glu Gln Cys Thr Thr Asn Ser Gly Glu Gln Ser
     50                  55                  60

Asp Gly Ser Ile Ala Trp Ser Val Glu Trp Ser Trp Thr Gly Gly Gln
 65                  70                  75                  80

Gly Gln Val Lys Ser Tyr Pro Asn Ala Val Val Glu Ile Glu Lys Lys
                 85                  90                  95

Thr Leu Gly Glu Val Ser Ser Ile Pro Ser Ala Trp Asp Trp Thr Tyr
             100                 105                 110

Thr Gly Asn Gly Ile Ile Ala Asn Val Ala Tyr Asp Leu Phe Thr Ser
         115                 120                 125

Ser Thr Glu Ser Gly Asp Ala Glu Tyr Glu Phe Met Ile Trp Leu Ser
130                 135                 140
```

```
Ala Leu Gly Gly Ala Gly Pro Ile Ser Asn Asp Gly Ser Pro Val Ala
145                 150                 155                 160

Thr Ala Glu Leu Ala Gly Thr Ser Trp Lys Leu Tyr Gln Gly Lys Asn
            165                 170                 175

Asn Gln Met Thr Val Phe Ser Phe Val Ala Glu Ser Asp Val Asn Asn
            180                 185                 190

Phe Cys Gly Asp Leu Ala Asp Phe Thr Asp Tyr Leu Val Asp Asn His
            195                 200                 205

Gly Val Ser Ser Gln Ile Leu Gln Ser Val Gly Ala Gly Thr Glu
    210                 215                 220

Pro Phe Glu Gly Thr Asn Ala Val Phe Thr Thr Asn Asn Tyr His Ala
225                 230                 235                 240

Asp Val Glu Tyr
```

<210> SEQ ID NO 44
<211> LENGTH: 250
<212> TYPE: PRT
<213> ORGANISM: Fusarium javanicum (2)

<400> SEQUENCE: 44

```
Met Lys Phe Phe Gly Val Val Ser Ala Ser Leu Ala Ala Thr Ala Val
1               5                   10                  15

Ala Thr Pro Thr Thr Pro Thr Glu Thr Ile Glu Lys Arg Asp Thr Thr
            20                  25                  30

Trp Cys Asp Ala Phe Gly Ser Leu Ala Thr Ser Gly Tyr Thr Val Tyr
            35                  40                  45

His Asn Asn Trp Gly Lys Gly Asp Ala Thr Ser Gly Ser Gln Cys Thr
    50                  55                  60

Thr Phe Thr Ser Val Ser Asn Asn Asn Phe Val Trp Ser Thr Ser Trp
65                  70                  75                  80

Thr Trp Ala Gly Gly Ala Gly Lys Val Lys Ser Tyr Ser Asn Val Ala
                85                  90                  95

Leu Glu Lys Ile Asn Lys Lys Ile Ser Asp Ile Lys Ser Val Ser Thr
            100                 105                 110

Arg Trp Ile Trp Arg Tyr Thr Gly Thr Lys Met Ile Ala Asn Val Ser
        115                 120                 125

Tyr Asp Leu Trp Phe Ala Pro Thr Ala Ser Ser Asn Asn Ala Tyr Glu
130                 135                 140

Ile Met Ile Trp Val Gly Ala Tyr Gly Gly Ala Leu Pro Ile Ser Thr
145                 150                 155                 160

Pro Gly Lys Gly Val Ile Asp Arg Pro Thr Leu Ala Gly Ile Pro Trp
                165                 170                 175

Asp Val Tyr Lys Gly Pro Asn Gly Asp Val Thr Val Ile Ser Phe Val
            180                 185                 190

Ala Ser Ser Asn Gln Gly Asn Phe Gln Ala Asp Leu Lys Glu Phe Leu
        195                 200                 205

Asn Tyr Leu Thr Ser Lys Gln Gly Leu Pro Ser Asn Tyr Val Ala Thr
210                 215                 220

Ser Phe Gln Ala Gly Thr Glu Pro Phe Glu Gly Thr Asn Ala Val Leu
225                 230                 235                 240

Lys Thr Ser Ala Tyr Thr Ile Ser Val Asn
                245                 250
```

<210> SEQ ID NO 45

```
<211> LENGTH: 238
<212> TYPE: PRT
<213> ORGANISM: Gliocladium roseum (1)

<400> SEQUENCE: 45

Met Lys Ala Asn Ile Val Ile Leu Ser Leu Phe Ala Pro Leu Ala Ala
1               5                   10                  15

Val Ala Gln Thr Leu Cys Gly Gln Tyr Ser Ser Asn Thr Gln Gly Gly
            20                  25                  30

Tyr Ile Phe Asn Asn Asn Met Trp Gly Met Gly Ser Gly Ser Gly Ser
        35                  40                  45

Gln Cys Thr Tyr Val Asp Lys Val Trp Ala Glu Gly Val Ala Trp His
    50                  55                  60

Thr Asp Trp Ser Trp Ser Gly Gly Asp Asn Asn Val Lys Ser Tyr Pro
65                  70                  75                  80

Tyr Ser Gly Arg Glu Leu Gly Thr Lys Arg Ile Val Ser Ser Ile Lys
                85                  90                  95

Ser Ile Ser Ser Gly Ala Asp Trp Asp Tyr Thr Gly Ser Asn Leu Arg
            100                 105                 110

Ala Asn Ala Ala Tyr Asp Ile Phe Thr Ser Ala Asn Pro Asn His Ala
        115                 120                 125

Thr Ser Ser Gly Asp Tyr Glu Val Met Ile Trp Leu Ala Asn Leu Gly
    130                 135                 140

Gly Leu Thr Pro Ile Gly Ser Pro Ile Gly Thr Val Lys Ala Ala Gly
145                 150                 155                 160

Arg Asp Trp Glu Leu Trp Asp Gly Tyr Asn Gly Ala Met Arg Val Tyr
                165                 170                 175

Ser Phe Val Ala Pro Ser Gln Leu Asn Ser Phe Asp Gly Glu Ile Met
            180                 185                 190

Asp Phe Phe Tyr Val Val Lys Asp Met Arg Gly Phe Pro Ala Asp Ser
        195                 200                 205

Gln His Leu Leu Thr Val Gln Phe Gly Thr Glu Pro Ile Ser Gly Ser
    210                 215                 220

Gly Ala Lys Phe Ser Val Ser His Trp Ser Ala Lys Leu Gly
225                 230                 235

<210> SEQ ID NO 46
<211> LENGTH: 348
<212> TYPE: PRT
<213> ORGANISM: Gliocladium roseum (2)

<400> SEQUENCE: 46

Met Lys Ser Ile Ile Ser Phe Phe Gly Leu Ala Thr Leu Val Ala Ala
1               5                   10                  15

Ala Pro Ser Gln Asn Pro Thr Arg Thr Gln Pro Leu Glu Lys Arg Ala
            20                  25                  30

Thr Thr Leu Cys Gly Gln Trp Asp Ser Val Glu Thr Gly Gly Tyr Thr
        35                  40                  45

Ile Tyr Asn Asn Leu Trp Gly Gln Asp Asn Gly Ser Gly Ser Gln Cys
    50                  55                  60

Leu Thr Val Glu Gly Val Thr Asp Gly Leu Ala Ala Trp Ser Ser Thr
65                  70                  75                  80

Trp Ser Trp Ser Gly Gly Ser Ser Val Lys Ser Tyr Ser Asn Ala
                85                  90                  95

Val Leu Ser Ala Glu Ala Ala Arg Ile Ser Ala Ile Ser Ser Ile Pro
            100                 105                 110
```

```
Ser Lys Trp Glu Trp Ser Tyr Thr Gly Thr Asp Ile Val Ala Asn Val
        115                 120                 125

Ala Tyr Asp Leu Phe Ser Asn Thr Asp Cys Gly Asp Thr Pro Glu Tyr
130                 135                 140

Glu Ile Met Ile Trp Leu Ser Ala Leu Gly Ala Gly Pro Ile Ser
145                 150                 155                 160

Ser Thr Gly Ser Ser Ile Ala Thr Val Thr Ile Ala Gly Ala Ser Trp
                165                 170                 175

Asn Leu Trp Gln Gly Gln Asn Asn Gln Met Ala Val Phe Ser Phe Val
            180                 185                 190

Ala Glu Ser Asp Gln Lys Ser Phe Ser Gly Asp Leu Asn Asp Phe Ile
        195                 200                 205

Gln Tyr Leu Val Asp Ser Gln Gly Tyr Ser Gly Ser Gln Cys Leu Tyr
        210                 215                 220

Ser Ile Gly Ala Gly Thr Glu Pro Phe Thr Gly Thr Asp Ala Glu Phe
225                 230                 235                 240

Ile Thr Thr Gly Tyr Ser Val Ser Val Ser Ala Gly Asp Ser Gly Cys
                245                 250                 255

Asp Glu Thr Thr Thr Ser Ser Gln Ala Gln Ser Ser Thr Val Glu Thr
            260                 265                 270

Ser Thr Ala Thr Gln Pro Gln Ser Ser Ser Thr Val Val Pro Thr Val
        275                 280                 285

Thr Leu Ser Gln Pro Ser Asn Glu Ser Thr Thr Thr Pro Val Gln Ser
        290                 295                 300

Gln Pro Ser Ser Val Glu Thr Thr Pro Thr Ala Gln Pro Gln Ser Ser
305                 310                 315                 320

Ser Val Gln Thr Thr Thr Thr Ala Gln Ala Gln Pro Thr Ser Gly Thr
                325                 330                 335

Gly Cys Ser Arg Arg Arg Lys Arg Ala Val Val
            340                 345

<210> SEQ ID NO 47
<211> LENGTH: 236
<212> TYPE: PRT
<213> ORGANISM: Gliocladium roseum (3)

<400> SEQUENCE: 47

Met Lys Phe Gln Leu Leu Ser Leu Thr Ala Phe Ala Pro Leu Ser Leu
1               5                   10                  15

Ala Ala Leu Cys Gly Gln Tyr Gln Ser Gln Ser Gln Gly Gly Tyr Ile
            20                  25                  30

Phe Asn Asn Asn Lys Trp Gly Gln Gly Ser Gly Ser Gly Ser Gln Cys
        35                  40                  45

Leu Thr Ile Asp Lys Thr Trp Asp Ser Asn Val Ala Phe His Ala Asp
    50                  55                  60

Trp Ser Trp Ser Gly Gly Thr Asn Asn Val Lys Ser Tyr Pro Asn Ala
65                  70                  75                  80

Gly Leu Glu Phe Ser Arg Gly Lys Lys Val Ser Ser Ile Gly Thr Ile
                85                  90                  95

Asn Gly Gly Ala Asp Trp Asp Tyr Ser Gly Ser Asn Ile Arg Ala Asn
            100                 105                 110

Val Ala Tyr Asp Ile Phe Thr Ser Ala Asp Pro Asn His Val Thr Ser
        115                 120                 125

Ser Gly Asp Tyr Glu Leu Met Ile Trp Leu Gly Lys Leu Gly Asp Ile
```

-continued

```
            130                 135                 140
Tyr Pro Ile Gly Asn Ser Ile Gly Arg Val Lys Ala Ala Asn Arg Glu
145                 150                 155                 160

Trp Asp Leu His Val Gly Tyr Asn Gly Ala Met Lys Val Phe Ser Phe
                    165                 170                 175

Val Ala Pro Ser Pro Val Thr Arg Phe Asp Gly Asn Ile Met Asp Phe
                180                 185                 190

Phe Tyr Val Met Arg Asp Met Gln Gly Tyr Pro Met Asp Lys Gln Tyr
            195                 200                 205

Leu Leu Ser Leu Gln Phe Gly Thr Glu Pro Phe Thr Gly Ser Asn Ala
        210                 215                 220

Lys Phe Ser Cys Trp Tyr Phe Gly Ala Lys Ile Lys
225                 230                 235
```

<210> SEQ ID NO 48
<211> LENGTH: 237
<212> TYPE: PRT
<213> ORGANISM: Gliocladium roseum (4)

<400> SEQUENCE: 48

```
Met Lys Thr Gly Ile Ala Tyr Leu Ala Ala Val Leu Pro Leu Ala Met
1               5                   10                  15

Ala Glu Ser Leu Cys Asp Gln Tyr Ala Tyr Leu Ser Arg Asp Gly Tyr
            20                  25                  30

Asn Phe Asn Asn Asn Glu Trp Gly Ala Ala Thr Gly Thr Gly Asp Gln
        35                  40                  45

Cys Thr Tyr Val Asp Ser Thr Ser Ser Gly Val Ser Trp His Ser
50                  55                  60

Asp Trp Thr Trp Ser Gly Ser Glu Ser Glu Ile Lys Ser Tyr Pro Tyr
65                  70                  75                  80

Ser Gly Leu Asp Leu Pro Glu Lys Lys Ile Val Thr Ser Ile Gly Ser
                85                  90                  95

Ile Ser Thr Gly Ala Glu Trp Ser Tyr Ser Gly Ser Asp Ile Arg Ala
            100                 105                 110

Asp Val Ala Tyr Asp Thr Phe Thr Ala Ala Asp Pro Asn His Ala Thr
        115                 120                 125

Ser Ser Gly Asp Tyr Glu Val Met Ile Trp Leu Ala Asn Leu Gly Gly
    130                 135                 140

Leu Thr Pro Ile Gly Ser Pro Ile Gly Thr Val Lys Ala Ala Gly Arg
145                 150                 155                 160

Asp Trp Glu Leu Trp Asp Gly Tyr Asn Gly Ala Met Arg Val Tyr Ser
                165                 170                 175

Phe Val Ala Pro Ser Gln Leu Asn Ser Phe Asp Gly Glu Ile Met Asp
            180                 185                 190

Phe Phe Tyr Val Val Lys Asp Met Arg Gly Phe Pro Ala Asp Ser Gln
        195                 200                 205

His Leu Leu Thr Val Gln Phe Gly Thr Glu Pro Ile Ser Gly Ser Gly
    210                 215                 220

Ala Lys Phe Ser Val Ser His Trp Ser Ala Lys Leu Gly
225                 230                 235
```

<210> SEQ ID NO 49
<211> LENGTH: 237
<212> TYPE: PRT
<213> ORGANISM: Memnoniella echinata

<400> SEQUENCE: 49

```
Met Lys Val Ala Ala Leu Leu Val Ala Leu Ser Pro Leu Ala Phe Ala
 1               5                  10                  15

Gln Ser Leu Cys Asp Gln Tyr Ser Tyr Tyr Ser Ser Asn Gly Tyr Glu
             20                  25                  30

Phe Asn Asn Asn Met Trp Gly Arg Asn Ser Gly Gln Gly Asn Gln Cys
         35                  40                  45

Thr Tyr Val Asp Tyr Ser Ser Pro Asn Gly Val Gly Trp Arg Val Asn
 50                  55                  60

Trp Asn Trp Ser Gly Gly Asp Asn Asn Val Lys Ser Tyr Pro Tyr Ser
 65                  70                  75                  80

Gly Arg Gln Leu Pro Thr Lys Arg Ile Val Ser Trp Ile Gly Ser Leu
             85                  90                  95

Pro Thr Thr Val Ser Trp Asn Tyr Gln Gly Asn Asn Leu Arg Ala Asn
             100                 105                 110

Val Ala Tyr Asp Leu Phe Thr Ala Ala Asn Pro Asn His Pro Asn Ser
             115                 120                 125

Ser Gly Asp Tyr Glu Leu Met Ile Trp Leu Gly Arg Leu Gly Asn Val
         130                 135                 140

Tyr Pro Ile Gly Asn Gln Val Ala Thr Val Asn Ile Ala Gly Gln Gln
145                 150                 155                 160

Trp Asn Leu Tyr Tyr Gly Tyr Asn Gly Ala Met Gln Val Tyr Ser Phe
                 165                 170                 175

Val Ser Pro Asn Gln Leu Asn Tyr Phe Ser Gly Asn Val Lys Asp Phe
             180                 185                 190

Phe Thr Tyr Leu Gln Tyr Asn Arg Ala Tyr Pro Ala Asp Ser Gln Tyr
         195                 200                 205

Leu Ile Thr Tyr Gln Phe Gly Thr Glu Pro Phe Thr Gly Gln Asn Ala
 210                 215                 220

Val Phe Thr Val Ser Asn Trp Ser Ala Gln Gln Asn Asn
225                 230                 235
```

<210> SEQ ID NO 50
<211> LENGTH: 246
<212> TYPE: PRT
<213> ORGANISM: Emericella desertoru

<400> SEQUENCE: 50

```
Met Lys Leu Leu Ala Leu Ser Leu Val Ser Leu Ala Ser Ala Ala Ser
 1               5                  10                  15

Ala Ala Ser Ile Leu Ser Asn Thr Phe Thr Arg Arg Ser Asp Phe Cys
             20                  25                  30

Gly Gln Trp Asp Thr Ala Thr Val Gly Asn Phe Ile Val Tyr Asn Asn
         35                  40                  45

Leu Trp Gly Gln Asp Asn Ala Asp Ser Gly Ser Gln Thr Gly Val Asp
 50                  55                  60

Ser Ala Asn Gly Asn Ser Ile Ser Trp His Thr Thr Trp Ser Trp Ser
 65                  70                  75                  80

Gly Gly Ser Ser Ser Val Lys Ser Tyr Ala Asn Ala Ala Tyr Gln Phe
             85                  90                  95

Thr Ser Thr Lys Leu Asn Ser Leu Ser Ser Ile Pro Thr Ser Trp Lys
             100                 105                 110

Trp Gln Tyr Ser Thr Thr Asp Ile Val Ala Asn Val Ala Tyr Asp Leu
         115                 120                 125
```

```
Phe Thr Ser Ser Ser Ala Gly Gly Asp Ser Glu Tyr Glu Ile Met Ile
        130                 135                 140

Trp Leu Ala Ala Leu Gly Gly Ala Gly Pro Ile Ser Ser Thr Gly Ser
145                 150                 155                 160

Ser Ile Ala Thr Val Thr Leu Gly Gly Val Thr Trp Ser Leu Tyr Ser
                165                 170                 175

Gly Pro Asn Gly Ser Met Gln Val Tyr Ser Phe Val Ala Ser Ser Thr
                180                 185                 190

Thr Glu Ser Phe Ser Ala Asp Leu Met Asp Phe Ile Asn Tyr Leu Ala
            195                 200                 205

Glu Asn Gln Gly Leu Ser Ser Gln Tyr Leu Thr His Val Gln Ala
        210                 215                 220

Gly Thr Glu Pro Phe Thr Gly Thr Asp Ala Thr Leu Thr Val Ser Ser
225                 230                 235                 240

Tyr Ser Val Ser Val Ser
                245
```

<210> SEQ ID NO 51
<211> LENGTH: 371
<212> TYPE: PRT
<213> ORGANISM: Actinomycete 11AG8

<400> SEQUENCE: 51

```
Met Arg Ser His Pro Arg Ser Ala Thr Met Thr Val Leu Val Val Leu
1               5                   10                  15

Ala Ser Leu Gly Ala Leu Leu Thr Ala Ala Pro Ala Gln Ala Asn
            20                  25                  30

Gln Gln Ile Cys Asp Arg Tyr Gly Thr Thr Ile Gln Asp Arg Tyr
        35                  40                  45

Val Val Gln Asn Asn Arg Trp Gly Thr Ser Ala Thr Gln Cys Ile Asn
50                  55                  60

Val Thr Gly Asn Gly Phe Glu Ile Thr Gln Ala Asp Gly Ser Val Pro
65                  70                  75                  80

Thr Asn Gly Ala Pro Lys Ser Tyr Pro Ser Val Tyr Asp Gly Cys His
                85                  90                  95

Tyr Gly Asn Cys Ala Pro Arg Thr Thr Leu Pro Met Arg Ile Ser Ser
                100                 105                 110

Ile Gly Ser Ala Pro Ser Ser Val Ser Tyr Arg Tyr Thr Gly Asn Gly
            115                 120                 125

Val Tyr Asn Ala Ala Tyr Asp Ile Trp Leu Asp Pro Thr Pro Arg Thr
130                 135                 140

Asn Gly Val Asn Arg Thr Glu Ile Met Ile Trp Phe Asn Arg Val Gly
145                 150                 155                 160

Pro Val Gln Pro Ile Gly Ser Pro Val Gly Thr Ala His Val Gly Gly
                165                 170                 175

Arg Ser Trp Glu Val Trp Thr Gly Ser Asn Gly Ser Asn Asp Val Ile
                180                 185                 190

Ser Phe Leu Ala Pro Ser Ala Ile Ser Ser Trp Ser Phe Asp Val Lys
            195                 200                 205

Asp Phe Val Asp Gln Ala Val Ser His Gly Leu Ala Thr Pro Asp Trp
        210                 215                 220

Tyr Leu Thr Ser Ile Gln Ala Gly Phe Glu Pro Trp Glu Gly Gly Thr
225                 230                 235                 240

Gly Leu Ala Val Asn Ser Phe Ser Ser Ala Val Asn Ala Gly Gly Gly
                245                 250                 255
```

```
Asn Gly Gly Thr Pro Gly Thr Pro Ala Ala Cys Gln Val Ser Tyr Ser
            260             265                 270

Thr His Thr Trp Pro Gly Gly Phe Thr Val Asp Thr Thr Ile Thr Asn
        275                 280                 285

Thr Gly Ser Thr Pro Val Asp Gly Trp Glu Leu Asp Phe Thr Leu Pro
    290                 295                 300

Ala Gly His Thr Val Thr Ser Ala Trp Asn Ala Leu Ile Ser Pro Ala
305                 310                 315                 320

Ser Gly Ala Val Thr Ala Arg Ser Thr Gly Ser Asn Gly Arg Ile Ala
                325                 330                 335

Ala Asn Gly Gly Thr Gln Ser Phe Gly Phe Gln Gly Thr Ser Ser Gly
            340                 345                 350

Thr Gly Phe Asn Ala Pro Ala Gly Gly Arg Leu Asn Gly Thr Ser Cys
        355                 360                 365

Thr Val Arg
    370

<210> SEQ ID NO 52
<211> LENGTH: 381
<212> TYPE: PRT
<213> ORGANISM: Streptomyces lividans CelB

<400> SEQUENCE: 52

Met Arg Thr Leu Arg Pro Gln Ala Arg Ala Pro Arg Gly Leu Leu Ala
1               5                   10                  15

Ala Leu Gly Ala Val Leu Ala Ala Phe Ala Leu Val Ser Ser Leu Val
            20                  25                  30

Thr Ala Ala Ala Pro Ala Gln Ala Asp Thr Thr Ile Cys Glu Pro Phe
        35                  40                  45

Gly Thr Thr Thr Ile Gln Gly Arg Tyr Val Val Gln Asn Asn Arg Trp
    50                  55                  60

Gly Ser Thr Ala Pro Gln Cys Val Thr Ala Thr Asp Thr Gly Phe Arg
65                  70                  75                  80

Val Thr Gln Ala Asp Gly Ser Ala Pro Thr Asn Gly Ala Pro Lys Ser
                85                  90                  95

Tyr Pro Ser Val Phe Asn Gly Cys His Tyr Thr Asn Cys Ser Pro Gly
            100                 105                 110

Thr Asp Leu Pro Val Arg Leu Asp Thr Val Ser Ala Ala Pro Ser Ser
        115                 120                 125

Ile Ser Tyr Gly Phe Val Asp Gly Ala Val Tyr Asn Ala Ser Tyr Asp
    130                 135                 140

Ile Trp Leu Asp Pro Thr Ala Arg Thr Asp Gly Val Asn Gln Thr Glu
145                 150                 155                 160

Ile Met Ile Trp Phe Asn Arg Val Gly Pro Ile Gln Pro Ile Gly Ser
                165                 170                 175

Pro Val Gly Thr Ala Ser Val Gly Gly Arg Thr Trp Glu Val Trp Ser
            180                 185                 190

Gly Gly Asn Gly Ser Asn Asp Val Leu Ser Phe Val Ala Pro Ser Ala
        195                 200                 205

Ile Ser Gly Trp Ser Phe Asp Val Met Asp Phe Val Arg Ala Thr Val
    210                 215                 220

Ala Arg Gly Leu Ala Glu Asn Asp Trp Tyr Leu Thr Ser Val Gln Ala
225                 230                 235                 240

Gly Phe Glu Pro Trp Gln Asn Gly Ala Gly Leu Ala Val Asn Ser Phe
```

-continued

```
                245                 250                 255
Ser Ser Thr Val Glu Thr Gly Thr Pro Gly Gly Thr Asp Pro Gly Asp
                    260                 265                 270

Pro Gly Gly Pro Ser Ala Cys Ala Val Ser Tyr Gly Thr Asn Val Trp
                275                 280                 285

Gln Asp Gly Phe Thr Ala Asp Val Thr Val Thr Asn Thr Gly Thr Ala
                290                 295                 300

Pro Val Asp Gly Trp Gln Leu Ala Phe Thr Leu Pro Ser Gly Gln Arg
305                 310                 315                 320

Ile Thr Asn Ala Trp Asn Ala Ser Leu Thr Pro Ser Ser Gly Ser Val
                    325                 330                 335

Thr Ala Thr Gly Ala Ser His Asn Ala Arg Ile Ala Pro Gly Gly Ser
                    340                 345                 350

Leu Ser Phe Gly Phe Gln Gly Thr Tyr Gly Gly Ala Phe Ala Glu Pro
                    355                 360                 365

Thr Gly Phe Arg Leu Asn Gly Thr Ala Cys Thr Thr Val
                    370                 375                 380

<210> SEQ ID NO 53
<211> LENGTH: 260
<212> TYPE: PRT
<213> ORGANISM: Rhodothermus marinus

<400> SEQUENCE: 53

Met Asn Val Met Arg Ala Val Leu Val Leu Ser Leu Leu Leu Leu Phe
1               5                   10                  15

Gly Cys Asp Trp Leu Phe Pro Asp Gly Asp Asn Gly Lys Glu Pro Glu
                20                  25                  30

Pro Glu Pro Glu Pro Thr Val Glu Leu Cys Gly Arg Trp Asp Ala Arg
                35                  40                  45

Asp Val Ala Gly Gly Arg Tyr Arg Val Ile Asn Asn Val Trp Gly Ala
                50                  55                  60

Glu Thr Ala Gln Cys Ile Glu Val Gly Leu Glu Thr Gly Asn Phe Thr
65                  70                  75                  80

Ile Thr Arg Ala Asp His Asp Asn Gly Asn Asn Val Ala Ala Tyr Pro
                    85                  90                  95

Ala Ile Tyr Phe Gly Cys His Trp Ala Pro Ala Arg Ala Ile Arg Asp
                    100                 105                 110

Cys Ala Ala Arg Ala Gly Ala Val Arg Arg Ala His Glu Leu Asp Val
                    115                 120                 125

Thr Pro Ile Thr Thr Gly Arg Trp Asn Ala Ala Tyr Asp Ile Trp Phe
                    130                 135                 140

Ser Pro Val Thr Asn Ser Gly Asn Gly Tyr Ser Gly Gly Ala Glu Leu
145                 150                 155                 160

Met Ile Trp Leu Asn Trp Asn Gly Gly Val Met Pro Gly Gly Ser Arg
                    165                 170                 175

Val Ala Thr Val Glu Leu Ala Gly Ala Thr Trp Glu Val Trp Tyr Ala
                    180                 185                 190

Asp Trp Asp Trp Asn Tyr Ile Ala Tyr Arg Arg Thr Thr Pro Thr Thr
                    195                 200                 205

Ser Val Ser Glu Leu Asp Leu Lys Ala Phe Ile Asp Asp Ala Val Ala
                    210                 215                 220

Arg Gly Tyr Ile Arg Pro Glu Trp Tyr Leu His Ala Val Glu Thr Gly
225                 230                 235                 240
```

```
                                    -continued
Phe Glu Leu Trp Glu Gly Gly Ala Gly Leu Arg Thr Ala Asp Phe Ser
                245                 250                 255

Val Thr Val Gln
            260

<210> SEQ ID NO 54
<211> LENGTH: 264
<212> TYPE: PRT
<213> ORGANISM: Erwinia carotovara

<400> SEQUENCE: 54

Met Gln Thr Val Asn Thr Gln Pro His Arg Ile Phe Arg Val Leu Leu
  1               5                  10                  15

Pro Ala Val Phe Ser Ser Leu Leu Ser Ser Leu Thr Val Ser Ala
                 20                  25                  30

Ala Ser Ser Ser Asn Asp Ala Asp Lys Leu Tyr Phe Gly Asn Asn Lys
                35                  40                  45

Tyr Tyr Leu Phe Asn Asn Val Trp Gly Lys Asp Glu Ile Lys Gly Trp
 50                  55                  60

Gln Gln Thr Ile Phe Tyr Asn Ser Pro Ile Ser Met Gly Trp Asn Trp
 65                  70                  75                  80

His Trp Pro Ser Ser Thr His Ser Val Lys Ala Tyr Pro Ser Leu Val
                 85                  90                  95

Ser Gly Trp His Trp Thr Ala Gly Tyr Thr Glu Asn Ser Gly Leu Pro
                100                 105                 110

Ile Gln Leu Ser Ser Asn Lys Ser Ile Thr Ser Asn Val Thr Tyr Ser
                115                 120                 125

Ile Lys Ala Thr Gly Thr Tyr Asn Ala Ala Tyr Asp Ile Trp Phe His
                130                 135                 140

Thr Thr Asp Lys Ala Asn Trp Asp Ser Ser Pro Thr Asp Glu Leu Met
145                 150                 155                 160

Ile Trp Leu Asn Asp Thr Asn Ala Gly Pro Ala Gly Asp Tyr Ile Glu
                165                 170                 175

Thr Val Phe Leu Gly Asp Ser Ser Trp Asn Val Phe Lys Gly Trp Ile
                180                 185                 190

Asn Ala Asp Asn Gly Gly Gly Trp Asn Val Phe Ser Phe Val His Thr
                195                 200                 205

Ser Gly Thr Asn Ser Ala Ser Leu Asn Ile Arg His Phe Thr Asp Tyr
                210                 215                 220

Leu Val Gln Thr Lys Gln Trp Met Ser Asp Glu Lys Tyr Ile Ser Ser
225                 230                 235                 240

Val Glu Phe Gly Thr Glu Ile Phe Gly Gly Asp Gly Gln Ile Asp Ile
                245                 250                 255

Thr Glu Trp Arg Val Asp Val Lys
                260
```

We claim:

1. A variant *T. reesei* EGIII cellulase (SEQ ID NO:31) comprising a substitution at a residue which is sensitive to temperature, selected for the group consisting of W7, A35, H45, S63, S77, M79, H108, Y147, M154, T163, and/or N167 in EGIII.

2. The cellulase of claim 1, wherein said variant comprises a substitution at a position corresponding to one or more of residues W7Y, A35V, H45Q, S63V, S77G, M79I, H108R, Y147W, M154N, T163S, and/or N167S.

3. A detergent composition comprising a surfactant and a variant EGIII cellulase consisting of a substitution at a position corresponding to one or more residues selected from the group consisting of W7, A35, H45, S63, S77, M79, H108, 147, M154, T163, and/or N167 in EGIII (SEQ ID NO:31).

4. The detergent of claim 3, wherein said variant EGIII cellulase comprises a substitution at a position corresponding to one or more of residues at position W7Y, A35V, H45Q, S63V, S77G, M79I, H108R, Y147W, M154N, T163S, and/or N167S.

5. The detergent according to claim 3, wherein said detergent is a laundry detergent.

6. The detergent according to claim 3, wherein said detergent is a dish detergent.

7. A method of treating a cellulose containing textile comprising contacting said textile with a variant EGIII cellulase according to claim 1.

8. A feed additive comprising a variant EGIII cellulase according to claim 1.

9. A method of treating wood pulp comprising contacting said wood pulp with a variant EGIII cellulase according to claim 1.

10. A method of converting biomass to glucose compressing contacting said biomass with a variant EGIII cellulase according to claim 1.

11. The method of claim 7, wherein the treatment is stonewashing of indigo dyed denim.

* * * * *